US010231993B2

(12) United States Patent
Pun et al.

(10) Patent No.: US 10,231,993 B2
(45) Date of Patent: Mar. 19, 2019

(54) BIOCOMPATIBLE POLYMERIC SYSTEM FOR TARGETED TREATMENT OF THROMBOTIC AND HEMOSTATIC DISORDERS

(71) Applicant: UNIVERSITY OF WASHINGTON THROUGH ITS CENTER FOR COMMERCIALIZATION, Seattle, WA (US)

(72) Inventors: Suzie H. Pun, Seattle, WA (US); Leslie Chan, Seattle, WA (US); Nathan J. White, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 14/392,359

(22) PCT Filed: Jun. 27, 2014

(86) PCT No.: PCT/US2014/044717

§ 371 (c)(1),
(2) Date: Dec. 23, 2015

(87) PCT Pub. No.: WO2014/210546

PCT Pub. Date: Dec. 31, 2014

(65) Prior Publication Data

US 2016/0263148 A1 Sep. 15, 2016

Related U.S. Application Data

(60) Provisional application No. 61/840,310, filed on Jun. 27, 2013.

(51) Int. Cl.

| | |
|---|---|
| ***A61K 38/00*** | (2006.01) |
| ***A61K 31/787*** | (2006.01) |
| ***A61K 38/36*** | (2006.01) |
| ***C07K 14/00*** | (2006.01) |
| ***A61K 9/00*** | (2006.01) |

(52) U.S. Cl.

CPC .......... *A61K 31/787* (2013.01); *A61K 9/0019* (2013.01); *A61K 38/36* (2013.01); *C07K 14/00* (2013.01)

(58) Field of Classification Search

None

See application file for complete search history.

(56) References Cited

U.S. PATENT DOCUMENTS

| | | | |
|---|---|---|---|
| 4,603,112 | A | 7/1986 | Paoletti et al. |
| 4,777,127 | A | 10/1988 | Suni et al. |
| 4,897,268 | A | 1/1990 | Tice et al. |
| 5,017,487 | A | 5/1991 | Stunnenberg et al. |
| 5,075,109 | A | 12/1991 | Tice et al. |
| 6,991,775 | B2 | 1/2006 | Koerner et al. |
| 7,015,194 | B2 | 3/2006 | Kjalke |
| 7,078,479 | B2 | 7/2006 | Rojkjaer |
| 7,125,846 | B2 | 10/2006 | Rojkjaer |
| 7,238,341 | B2 | 7/2007 | Zhang et al. |
| 7,927,581 | B2 | 4/2011 | Zhang et al. |
| 7,939,288 | B2 | 5/2011 | Wrabetz et al. |
| 8,026,214 | B2 | 9/2011 | Jensen et al. |
| 8,394,768 | B2 | 3/2013 | Dickneite |
| 8,466,107 | B2 | 6/2013 | Bussat et al. |
| 8,575,104 | B2 | 11/2013 | Weimer et al. |
| 8,580,737 | B2 | 11/2013 | Dickneite |
| 8,603,979 | B2 | 12/2013 | Dickneite et al. |
| 8,618,263 | B2 | 12/2013 | Hilden et al. |
| 2002/0197302 | A1 | 12/2002 | Cochrum et al. |
| 2003/0180222 | A1 | 9/2003 | Zhang et al. |
| 2003/0216320 | A1 | 11/2003 | Koerner et al. |
| 2005/0074411 | A1 | 4/2005 | Zhang et al. |
| 2006/0039861 | A1 | 2/2006 | Zhang et al. |
| 2007/0185311 | A1 | 8/2007 | Zhang et al. |

(Continued)

FOREIGN PATENT DOCUMENTS

| | | | |
|---|---|---|---|
| CA | 2455638 | C | 1/2013 |
| CN | 1599577 | A | 3/2005 |

(Continued)

OTHER PUBLICATIONS

Borgman et al. Mol Pharm. 2009 ; 6(6): 1836-1847.*
Tao et al. Biomacromolecules, vol. 10, No. 10, 2009.*
Smith et al. (Conjugation of Arginine-Glycine-Aspartic Acid Peptides to Thermoreversible N-isopropylacrylamide Polymers, Journal of Polymer Science: Part A: Polymer Chemistry, vol. 41, 3989-4000 (2003).*
Hagemo, JS et al. (Jul. 2013) "Changes in fibrinogen availability and utilization in an animal model of traumatic coagulopathy," Scandinavian Journal of Trauma, Resuscitation and Emergency Medicine, 21:56.
Hawiger, J (Feb. 1987) "Formation and regulation of platelet and fibrin hemostatic plug," Human Pathology, 18(2):111-122.
Hein, J. (1990; retrieved May 2016) "Unified Approach to Alignment and Phylogenes," Methods in Enzymology, 183:626-645.

(Continued)

*Primary Examiner* — Jeanette M Lieb
(74) *Attorney, Agent, or Firm* — Christensen O'Connor Johnson Kindness PLLC

(57) ABSTRACT

A biocompatible polymer to which a plurality of clot-modulating peptides (CMPs) are bound. The polymer comprises repeating units of hydrophilic monomers and display monomers to which the CMPs are bound. For example, the CMPs can be fibrin binding peptides (FBPs) that enhance clot formation by cross-linking that occurs within and between fibers by the plurality of fibrin-binding peptides during fibrin polymerization. The polymers of the invention can be used to modulate clotting in a variety of ways via multivalent display of fibrin-binding peptides and other clot-binding and clot-modulating moieties on polymer or co-polymer backbones. In addition to clot-modulating moieties, imaging agents and therapeutic agents can be conjugated to the polymers to facilitate imaging of blood flow and thrombosis, and for treatment of clotting-related disorders.

29 Claims, 10 Drawing Sheets

Specification includes a Sequence Listing.

(56) References Cited

U.S. PATENT DOCUMENTS

2009/0221680 A1* 9/2009 Diener ................ C12N 15/115 514/44 R
2009/0235339 A1 9/2009 Mennes et al.
2011/0250284 A1 10/2011 Lavik et al.
2012/0082987 A1 4/2012 Sasgary et al.
2012/0328512 A1 12/2012 Bussat

FOREIGN PATENT DOCUMENTS

| | | | |
|---|---|---|---|
| EP | 0345242 | A2 | 12/1989 |
| EP | 2235188 | A2 | 10/2010 |
| EP | 1420681 | B1 | 12/2013 |
| GB | 2200651 | A | 8/1988 |
| WO | WO89/01973 | A2 | 3/1989 |
| WO | WO91/02805 | A2 | 3/1991 |
| WO | WO2003/011115 | A3 | 5/2003 |
| WO | WO2007/024393 | A2 | 3/2007 |
| WO | WO2008/019381 | A1 | 2/2008 |
| WO | WO2008071679 | * | 6/2008 |
| WO | WO2008/103345 | A2 | 8/2008 |
| WO | WO2009/067562 | A1 | 5/2009 |
| WO | WO2009/088876 | A2 | 7/2009 |
| WO | WO2011/135308 | A1 | 11/2011 |
| WO | WO2012142362 | A2 | 10/2012 |

OTHER PUBLICATIONS

Hennink, WE et al. (Jan. 2002) "Novel crosslinking methods to design hydrogels," Advanced Drug Delivery Reviews, 54(1):13-36.

Hethershaw, EL et al. (Feb. 2014) "The effect of blood coagulation factor XIII on fibrin clot structure and fibrinolysis," Journal of Thrombosis and Haemostasis, 12(2):197-205.

Higgins, DG et al. (Apr. 1989) "Fast and sensitive multiple sequence alignments on a microcomputer," Computer applications in the Biosciences, 5(2):151-153.

Holcomb, JB et al. (Sep. 2008) "Increased plasma and platelet to red blood cell ratios improves outcome in 466 massively transfused civilian trauma patients," Annals of Surgery, 248(3):447-458.

Horton, JD et al. (May 2008) "Use of rFVIIa in the trauma setting—practice patterns in United States trauma centers," The American Surgeon, 74(5):413-417.

Hunt, BJ (Feb. 2014) "Bleeding and coagulopathies in critical care," New England Journal of Medicine, 370(9):847-859.

Jena, AK et al. (Jul. 1999) "In-plane compression porometry of battery separators," Journal of Power Sources, 80(1-2):46-52.

Jena, AK et al. (Summer 2005) "Pore Volume of Nanofiber Nonwovens," Journal of Engineered Fibers and Fabrics, pp. 25-30.

Jin, H-J et al. (Nov. 2013) "Urokinase-coated chitosan nanoparticles for thrombolytic therapy: preparation and pharmacodynamics in vivo," Journal of Thrombosis and Thrombolysis, 36(4):458-468.

Johansson, PI et al. (Mar. 2010) "Hypocoagulability, as evaluated by thrombelastography, at admission to the ICU is associated with increased 30-day mortality," Blood Coagulation & Fibrinolysis, 21(2):168-174.

Jones, SW et al. (Jul. 2013) "Nanoparticle clearance is governed by Th1/Th2 immunity and strain background," Journal of Clinical Investigation, 123(7):3061-3073.

Kass-Eisler, A et al. (Dec. 1993) "Quantitative determination of adenovirus-mediated gene delivery to rat cardiac myocytes in vitro and in vivo," Proceedings of the National Academy of Sciences USA, 90(24):11498-11502.

Kauvar, DS et al. (Jun. 2006) "Impact of hemorrhage on trauma outcome: an overview of epidemiology, clinical presentations, and therapeutic considerations," Journal of Trauma. 60(6 Suppl):S3-11.

Kheirabadi, BS et al. (Sep. 2009) "Determination of efficacy of new hemostatic dressings in a model of extremity arterial hemorrhage in swine," Journal of Trauma, 67(3):450-459; discussion 459-460.

Klokkevold, PR et al. (Jan. 1999) "The Effect of Chitosan (poly-N-Acetyl Glucosamine) on Lingual Hemostasis in Heparinized Rabbits," Journal of Oral and Maxillofacial Surgery, 57(1):49-52.

Koksal, O et al. (May 2011) "Hemostatic effect of a chitosan linear polymer (Celox®) in a severe femoral artery bleeding rat model under hypothermia or warfarin therapy," Turkish Journal of Trauma & Emergency Surgery, 17(3):199-204.

Kolls, J et al. (Jan. 1994) "Prolonged and effective blockade of tumor necrosis factor activity through adenovirus-mediated gene transfer," Proceedings of the National Academy of Sciences USA, 91(1):215-219.

Kolodziej, AF et al. (Oct. 2013) "Peptide Optimization and Conjugation Strategies in the Development of Molecularly Targeted Magnetic Resonance Imaging Contract Agents," in AE Nixon (ed.), Therapeutic Peptides: Methods and Protocols, Methods in Molecular Biology, 1088:185-211.

Kong, M et al. (Nov. 2010) "Antimicrobial properties of chitosan and mode of action: a state of the art review," International Journal of Food Microbiology, 144(1):51-63.

Kooistra, T. et al. (Jun. 1994) "Regulation of endothelial cell t-PA synthesis and release," International Journal of Hematology, 59(4):233-255.

Kozek-Langenecker, SA et al. (Jun. 2013) "Management of severe perioperative bleeding: guidelines from the European Society of Anaesthesiology," European Journal of Anaesthesiology, 30(6):270-382.

Kozen, B.G. et al. (Jan. 2008) "An alternative hemostatic dressing: comparison of CELOX, HemCon, and QuikClot," Academic Emergency Medicine, 15(1):74-81.

Laudano, AP et al. (Jul. 1978) "Synthetic peptide derivatives that bind to fibrinogen and prevent the polymerization of fibrin monomers," Proceedings of the National Academy of Sciences USA, 75(7):3085-3089.

Lee, DH, et al. (Sep. 2001) "Novel treatment modalities: new platelet preparations and substitutes," British Journal of Haematology, 114(3):496-505.

Lerner, EB et al. (Jul. 2001) "The golden hour: scientific fact or medical 'urban legend'?" Academic Emergency Medicine, 8(7):758-760.

Levi, M. et al. (Jan. 1999) "Fibrinogen-coated albumin microcapsules reduce bleeding in severely thrombocytopenic rabbits," Nature Medicine, 5(1):107-111.

Levy, JH et al. (May 2013) "Biology of Factor XIII and clinical manifestations of Factor XIII deficiency," Transfusion, 53(5):1120-1131.

Lim, B.B.C. et al. (Mar. 2008) "Molecular basis of fibrin clot elasticity," Structure, 16(3):449-459.

Lisman, T (Jan. 2002) "Inhibition of fibrinolysis by recombinant factor VIIa in plasma from patients with severe hemophilia A," Blood, 99(1):179-179.

Lord, ST (May 2007) "Fibrinogen and fibrin: scaffold proteins in hemostasis," Current Opinion in Hematology, 14(3):236-241.

Mammen, M. et al. (Nov. 1998) "Polyvalent interactions in biological systems: Implications for design and use of multivalent ligands and inhibitors," Angewandte Chemie International Edition, 37(20):2754-2794.

Merrifield, RB (Jul. 1963) "Solid Phase Peptide Synthesis. I. The Synthesis of a Tetrapeptide," Journal of the American Chemical Society, 85(14):2149-2154.

Mikhail, J (Feb. 1999) "The trauma triad of death: hypothermia, acidosis, and coagulopathy," AACN Clinical Issues, 10(1):85-94.

Modery, CL et al. (Dec. 2011) "Heteromultivalent liposomal nanoconstructs for enhanced targeting and shear-stable binding to active platelets for site-selective vascular drug delivery," Biomaterials, 32(35):9504-9514.

Modery-Pawlowski, CL. et al. (Jan. 2013) "Approaches to synthetic platelet analogs," Biomaterials, 34(2):526-541.

Morrison, JJ et al. (Feb. 2012) "Military Application of Tranexamic Acid in Trauma Emergency Resuscitation (MATTERs) Study," Archives of Surgery, 147(2):113-119.

Moss, B et al. (1989; accessed Nov. 2016) "Vaccinia virus expression vectors," Annals of the New York Academy of Sciences, 569:86-103.

Myers, EW et al. (Mar. 1988) "Optimal alignments in linear space," Computer Applications in the Biosciences, 4(1):11-17.

(56) References Cited

OTHER PUBLICATIONS

Nieuwenhuizen, L et al. (Jul. 2013) "Haemarthrosis stimulates the synovial fibrinolytic system in haemophilic mice," Thrombosis and Haemostasis, 110(1):173-183.
Nishijima, DK et al. (Nov. 2009) "Evidence-based Emergency Medicine/Critically Appraised Topic. The efficacy of recombinant activated factor VII in severe trauma," Annals of Emergency Medicine, 54(5):737-744.e1.
Nishiya, T et al. (Jul. 2002) "Reconstitution of adhesive properties of human platelets in liposomes carrying both recombinant glycoproteins Ia/IIa and Ib alpha under flow conditions: specific synergy of receptor-ligand interactions," Blood, 100(1):136-142.
Nishiya, T. et al. (Apr. 2000) "Targeting of liposomes carrying recombinant fragments of platelet membrane glycoprotein Ibα to immobilized von Willebrand factor under flow conditions," Biochemical and Biophysical Research Communications, 270(3):755-760.
Nishiya, T. et al. (Nov. 2001) "Platelet interactions with liposomes carrying recombinant platelet membrane glycoproteins or fibrinogen: approach to platelet substitutes," Artificial Cells, Blood Substitutes, and Immobilization Biotechnology, 29(6):453-464.
Novo Nordisk Canada Inc. (Apr. 2014; retrieved May 2016) "Tretten (catridecacog)—A recombinant factor XIII A-subunit," available online at: http://www.blood.ca/CentreApps/Intemet/UW_V502_MainEngine.nsf/resources/CustomerLetters2013/$file/Tretten-DoseRefCard.pdf.
Nystrup, KB et al. (Sep. 2011) "Reduced clot strength upon admission, evaluated by thrombelastography (TEG), in trauma patients is independently associated with increased 30-day mortality," Scandinavian Journal of Trauma, Resuscitation and Emergency Medicine, 19:52.
Odom, SR et al. (Apr. 2013) "Lactate clearance as a predictor of mortality in trauma patients," Journal of Trauma and Acute Care Surgery, 74(4):999-1004.
Okamura Y et al. (Jun. 2008) "Haemostatic effects of polymerized albumin particles carrying fibrinogen gamma-chain dodecapeptide as platelet substitutes in severely thrombocytopenic rabbits," Transfusion Medicine, 18(3):158-166.
Okamura, Y et al. (Jul. 2005) "Hemostatic effects of fibrinogen gamma-chain dodecapeptide-conjugated polymerized albumin particles in vitro and in vivo," Transfusion, 45(7):1221-1228.
Okamura, Y et al. (Mar. 2009) "Development of fibrinogen gamma-chain peptide-coated, adenosine diphosphate-encapsulated liposomes as a synthetic platelet substitute," Journal of Thrombosis and Haemostasis, 7(3):470-477.
Okamura, Y et al. (Nov.-Dec. 2005) "Hemostatic effects of phospholipid vesicles carrying fibrinogen gamma chain dodecapeptide in vitro and in vivo," Bioconjugate Chemistry, 16(6):1589-1596.
Okamura, Y. et al. (Jul. 2007) "Prolonged hemostatic ability of polyethylene glycol-modified polymerized albumin particles carrying fibrinogen gamma-chain dodecapeptide," Transfusion, 47(7):1254-1262.
Putnam, DA (Jun. 2006) "Polymers for gene delivery across length scales," Nature Materials, 5(6):439-451.
Rall, J.M. et al. (Aug. 2013) "Comparison of novel hemostatic dressings with QuikClot combat gauze in a standardized swine model of uncontrolled hemorrhage," Journal of Trauma and Acute Care Surgery, 75(2 Suppl 2): S150-S156.
Rao, SB, et al. (Jan. 1997) "Use of chitosan as a biomaterial: studies on its safety and hemostatic potential," Journal of Biomedical Materials Research, 34(1):21-28.
Ravikumar, M. et al. (Jun. 2012) "Mimicking Adhesive Functionalities of Blood Platelets using Ligand-Decorated Liposomes," Bioconjugate Chemistry, 23(6):1266-1275.
Rawal, A. et al. (Jun. 2009) "Predicting the properties of needlepunched nonwovens using artificial neural network," Journal of Applied Polymer Science, 112(6):3575-3581.
Raza, I et al. (Feb. 2013) "The incidence and magnitude of fibrinolytic activation in trauma patients," Journal of Thrombosis and Haemostasis, 11(2):307-314.
Rizoli, SB et al. (2006; accessed Nov. 2016) "Recombinant activated factor VII as an adjunctive therapy for bleeding control in severe trauma patients with coagulopathy: subgroup analysis from two randomized trials," Critical Care, 10(6):R178.
Robinson, DF, (Oct. 1971) "Comparison of labeled trees with valency three," Journal of Combinatorial Theory, Series B, 11(2):105-119.
Roche, AM et al. (Apr. 2006) "A head-to-head comparison of the in vitro coagulation effects of saline-based and balanced electrolyte crystalloid and colloid intravenous fluids," Anesthesia and Analgesia, 102(4):1274-1279.
Rolland, AP (1998; accessed Nov. 2016) "From genes to gene medicines: recent advances in nonviral gene delivery," Critical Reviews in Therapeutic Drug Carrier Systems, 15(2):143-198.
Rosenfeld, MA et al. (Apr. 1991) "Adenovirus-mediated transfer of a recombinant alpha 1-antitrypsin gene to the lung epithelium in vivo," Science, 252(5004):431-434.
Rybak, ME et al. (1993; epub Jul. 2009) "A liposome based platelet substitute, the plateletsome, with hemostatic efficacy," Biomaterials, Artificial Cells, and Immobilization Biotechnology, 21(2):101-118.
Saitou, N et al. (Jul. 1987) "The neighbor-joining method: a new method for reconstructing phylogenetic trees," Molecular Biology and Evolution, 4(4):406-425.
Sauaia A et al. (Feb. 1995) "Epidemiology of trauma deaths: a reassessment," The Journal of Trauma: Injury, Infection, and Critical Care, 38(2):185-193.
Schenone, M. et al. (Jul. 2004) "The blood coagulation cascade," Current Opinion in Hematology, 11(4):272-277.
Schense, JC et al. (Jan.-Feb. 1999) "Cross-linking Exogenous Bifunctional Peptide into Fibring Gels with Factor XIIIa," Bioconjugate Chemistry, 10(1):75-81.
Schöchl, H. et al. (Nov. 2014) "Trauma bleeding management: The concept of goal-directed primary care," Anesthesia and Analgesia, 119(5):1064-1073.
Schreiber, MA (Dec. 2005) "Coagulopathy in the trauma patient," Current Opinion in Critical Care, 11(6):590-597.
Shakur, H. et al. (Jul. 2010) "Effects of tranexamic acid on death, vascular occlusive events, and blood transfusion in trauma patients with significant haemorrhage (CRASH-2): a randomised, placebo-controlled trial," Lancet, 376(9734):23-32.
Shenkman, B. et al. (Jul. 2012) "The in-vitro effect of fibrinogen, factor XIII and thrombin-activatable fibrinolysis Inhibitor on clot formation and susceptibility to tissue plasminogen activator-induced fibrinolysis in hemodilution model," Blood Coagulation & Fibrinolysis, 23(5):370-378.
Shin, M.-F. et al. (Dec. 2006) "Platelet adsorption and hemolytic properties of liquid crystal/composite polymers," International Journal of Pharmaceutics, 327(1-2):117-125.
Shoffstall, AJ et al. (Aug. 2013) "Tuning Ligand Density on Intravenous Hemostatic Nanoparticles Dramatically Increases Survival Following Blunt Trauma," Biomacromolecules, 14(8):2790-2797.
Shoffstall, AJ et al. (Nov. 2012) "Intravenous hemostatic nanoparticles increase survival following blunt trauma Injury," Biomacromolecules, 13(11):3850-3857.
Sihler, KC et al. (Jan. 2010) "Complications of massive transfusion," Chest, 137(1):209-220.
Šimor, M. et al. (Jul. 2003) "Atmospheric-pressure plasma treatment of polyester nonwoven fabrics for electroless plating," Surface and Coatings Technology, 172(1):1-6.
Smith, A.H. et al. (epub Nov. 2012) "Haemostatic dressings in prehospital care," Emergency Medicine Journal, 30(10):784-789.
Soon, ASC et al. (Mar. 2010) "Engineering fibrin matrices: the engagement of polymerization pockets through fibrin knob technology for the delivery and retention of therapeutic proteins," Biomaterials, 31(7):1944-1954.
Spahn, DR et al. (Apr. 2013) "Management of bleeding and coagulopathy following major trauma: an updated European guideline," Critical Care, 17(2):R76.
Stinger, HK et al. (Feb. 2008) "The ratio of fibrinogen to red cells transfused affects survival in casualties receiving massive transfu-

(56) References Cited

OTHER PUBLICATIONS sions at an army combat support hospital," The Journal of Trauma, 64(2 Suppl):S79-S85; discussion S85.
Swaroop, M. et al. (Jan. 2013) "Pre-hospital transport times and survival for Hypotensive patients with penetrating thoracic trauma," Journal of Emergencies, Trauma, and Shock, 6(1):16-20.
Ta, H.T. et al. (Mar. 2008) "Injectable chitosan hydrogels for localised cancer therapy," Journal of Controlled Release, 126(3):205-216.
Takeoka, S et al. (Aug. 2002) "Rolling properties of rGPIbalpha-conjugated phospholipid vesicles with different membrane flexibilities on vWf surface under flow conditions," Biochemical and Biophysical Research Communications, 296(3):765-770.
Theusinger, OM et al. (Aug. 2010) "In vitro factor XIII supplementation increases clot firmness in Rotation Thromboelastometry (ROTEM)," Thrombosis and Haemostasis, 104(2):385-391.
U.S. Food and Drug Adminsitration (Dec. 2013) "FDA approves Tretten to treat rare genetic clotting disorder," [Press Release] available online at: http://www.fda.gov/newsevents/newsroom/pressannouncements/ucm379696.htm.
Ulmer, JB et al. (Mar. 1993) "Heterologous protection against influenza by injection of DNA encoding a viral protein," Science, 259(5102):1745-1749.
Wang, Y. et al. (Apr. 2009) "Surface characterization of the chitosan membrane after oxygen plasma treatment and its aging effect," Biomedical Materials, 4(3):035003.
Wedmore, I. et al. (Mar. 2006) "A special report on the chitosan-based hemostatic dressing: experience in current combat operations," Journal of Trauma, 60(3):655-658.
White, NJ (Apr. 2013) "Improved survival with less bleeding during limited resuscitation of uncontrolled hemorrhagic shock with fibrinogen concentrate as hemostatic agent [Abstract]," Annual Scientific Meeting for the Society of Emergency Medicine, 1 page.
Wilbur, WJ et al. (Feb. 1983) "Rapid similarity searches of nucleic acid and protein data banks," Proceedings of the National Academy of Sciences USA, 80(3):726-730.
Wufsus, AR et al. (Apr. 2013) "The hydraulic permeability of blood clots as a function of fibrin and platelet density," Biophysical Journal, 104(8):1812-1823.
Yamaoka, T. et al. (Apr. 1994) "Distribution and tissue uptake of poly(ethylene glycol) with different molecular weight after intravenous administration to mice," Journal of Pharmaceutical Sciences, 83(4):601-606.
Huang J. et al. Biocomposites of pHEMA with HA/β-TCP (60/40) for bone tissue engineering: Swelling, hydrolytic degradation, and in vitro behavior. Polymer (Guildf)., Feb. 5, 2013;54(3):1197-1207. doi:10.1016/j.polymer.2012.12.045, p. 1-25, table 1.
Johnson, Russell N., et al., Biological Activity of Anti-CD20 Multivalent HPMA Copolymer-Fab Conjugates. Biomacromolecules. Mar. 12, 2012; 13(3): 727-735. doi:10.1021/bm201656k.
Kolodziej, Andrew F., et al., Fibrin Specific Peptides Derived by Phage Display: Characterization of Peptides and Conjugates for Imaging. Bioconjugate Chem. 2012, 23, 548-556. dx.doi.org/10.1021/bc200613e.
Larsen, D.M. et al., Variability in platelet- and collagen-binding defects in type 2M von Willebrand disease. Haemophilia., Jul. 2013;19(4):590-594. Article first published online: Mar. 18, 2013. doi: 10. 1111/hae.12117, p. 1-11.
Lorand, Laszlo, et al., A double-headed Gly-Pro-Arg-Pro ligand mimics the functions of the E domain of fibrin for promoting the end-to-end crosslinking of gamma chains by factor XIIIa. PNAS Biochemistry, vol. 95, pp. 537-541, Jan. 1998.
Overoye-Chan, et al., EP-2104R: A Fibrin-Specific Gadolinium-Based MRI Contrast Agent for Detection of Thrombus. J. Am. Chem. Soc. 2008, 130, 6025-6039.
Soon, Allyson S.C. et al., Modulation of fibrin matrix properties via knob:hole affinity interactions using peptide-PEG conjugates. Biomaterials. Jul. 2011 ; 32(19):4406-4414. doi:10.1016/j.biomaterials.2011.02.050.
Stabenfeldt, Sarah E. et al., A new direction for anticoagulants: Inhibiting fibrin assembly with PEGylated fibrin knob mimics. Biotechnol Bioeng. PMC, Oct. 21, 2012.
Vymazal, Josef, et al.,Thrombus Imaging With Fibrin-Specific Gadolinium-Based MR Contrast Agent EP-2104R: Results of a Phase II Clinical Study of Feasibility. Investigative Radiology, Nov. 2009, 44(11):697-704.
Weisel, John W., et al., Mechanisms of fibrin polymerization and clinical implications. Blood, 2013 121(10):1712-1719. doi:10.1182/blood-2012-09-306639.
Yanjarappa, M.J.; Gujraty, et al., Synthesis of copolymers containing an active ester of methacrylic acid by RAFT: Controlled molecular weight scaffolds for biofunctionalization. Biomacromolecules 2006, 7, 1665-1670.
International Search Report and Written Opinion dated Oct. 30, 2014 from corresponding International Application PCT/US14/044717 filed Jun. 27, 2014 (WO2014210546).
Achneck, HE et al. (Feb. 2010) "A comprehensive review of topical hemostatic agents: efficacy and recommendations for use," Annals of Surgery, 251(2):217-228.
Adelman, JP et al. (1983; accessed Nov. 2016) "In vitro deletional mutagenesis for bacterial production of the 20,000-dalton form of human pituitary growth hormone," DNA, 2(3):183-193.
Arnaud, F. et al. (Oct. 2009) "Comparison of 10 hemostatic dressings in a groin transection model in swine," Journal of Trauma, 67(4):848-855.
Azuma, K et al. (Jan. 2015) "Anticancer and anti-inflammatory properties of chitin and chitosan oligosaccharides," Journal of Functional Biomaterials, 6(1):33-49.
Baldrick, P et al. (Apr. 2010) "The safety of chitosan as a pharmaceutical excipient," Regulatory Toxicology and Pharmacology, 56(3):290-299.
Barrett, GD et al. (Nov. 1986) "Clinical results of hydrogel lens implantation," Journal of Cataract and Refractive Surgery, 12(6):623-631.
Bennett, BL et al. (May 2014) "Review of new topical hemostatic dressings for combat casualty care," Military Medicine, 179(5):497-514.
Berkner, KL (Jul.-Aug. 1988) "Development of adenovirus vectors for the expression of heterologous genes," Biotechniques, 6(7):616-629.
Bertram, JP et al. (Dec. 2009) "Intravenous hemostat: nanotechnology to halt bleeding," Science Translational Medicine, 1(11):11ra22.
Boffard, KD et al. (Jul. 2005) "Recombinant factor VIIa as adjunctive therapy for bleeding control in severely injured trauma patients: two parallel randomized, placebo-controlled, double-blind clinical trials," The Journal of Trauma, 59(1):8-15; discussion 15-18.
Brohi, K et al. (Dec. 2007) "Acute coagulopathy of trauma: mechanism, identification and effect," Current Opinion in Critical Care, 13(6):680-685.
Brohi, K et al. (Jun. 2003) "Acute traumatic coagulopathy," The Journal of Trauma: Injury, Infection, and Critical Care, 54(6):1127-1130.
Cap, AP et al. (Jul. 2011) "Tranexamic acid for trauma patients: a critical review of the literature," The Journal of Trauma, 71(1 Suppl):S9-S14.
Carr Jr., ME et al. (Jan.-Feb. 1978) "Size and density of fibrin fibers from turbidity," Macromolecules, 11(1):46-50.
Carr Jr., ME et al., (Nov. 1987) "Fibrin has larger pores when formed in the presence of erythrocytes," American Journal of Physiology, 253(5 Pt 2):H1069-H1073.
Černáková, L. et al. (Aug. 2005) "Surface Modification of Polypropylene Non-Woven Fabrics by Atmospheric-Pressure Plasma Activation Followed by Acrylic Acid Grafting," Plasma Chemistry and Plasma Processing, 25(4):427-437.
Chan, LW et al. (Feb. 2016) "PolySTAT-Modified Chitosan Gauzes for Improved Hemostasis in External Hemorrhage," Acta Biomaterialia, 31:178-185.
Chan, LW et al. (Mar. 2015) "A Synthetic Fibrin-Crosslinking Polymer for Modulating Clot Properties and Inducing Hemostasis," Science Translational Medicine, 7(277):277ra29.

(56) References Cited

OTHER PUBLICATIONS

Chernysh, IN et al. (2012; accessed Dec. 2016) "Fibrin clots are equilibrium polymers that can be remodeled without proteolytic digestion," Scientific Reports, 2:879.
Cohen, J (Mar. 1993) "Naked DNA points way to vaccines," Science, 259(5102):1691-1692.
Coller, BS et al. (Feb. 1992) "Thromboerythrocytes. In vitro studies of a potential autologous, semi-artificial alternative to platelet transfusions," The Journal of Clinical Investigation, 89(2):546-555.
Collet, JP et al. (May 2000) "Influence of fibrin network conformation and fibrin fiber diameter on fibrinolysis speed: dynamic and structural approaches by confocal microscopy," Arteriosclerosis, Thrombosis and Vascular Biology, 20(5):1354-1361.
Croisier, F. et al., (Apr. 2013) "Chitosan-based biomaterials for tissue engineering," European Polymer Journal, 49(4):780-792.
Cushing M. et al. (Mar. 2011) "Blood transfusion in trauma patients: unresolved questions," Minerva Anestesiologica, 77(3):349-359.
Daniel, JL et al. (Jan. 1998) "Molecular basis for ADP-induced platelet activation. I. Evidence for three distinct ADP receptors on human platelets," The Journal of Biological Chemistry, 273:2024-2029.
Darlington, DN et al. (May 2013) "Acute coagulopathy of trauma in the rat," Shock, 39(5):440-446.
Davenport, R et al. (Dec. 2011) "Functional definition and characterization of acute traumatic coagulopathy," Critical Care Medicine, 39(12):2652-2658.
Dayhoff, MO (1978; retrieved May 2016) "A model of evolutionary change in protein—Matrices for detecting distant relationships," in MO Dayhoff (ed.), Atlas of Protein Sequence and Structure, National Biomedical Research Foundation, Washington, DC, 5(Suppl 3):345-352.
Devine, DV et al., (Jul. 2010) "Processing of whole blood into cellular components and plasma," ISBT Sciences Series, 5(1):78-82.
Devlin, J.J. et al. (Sep. 2011) "Comparison of ChitoFlex®, Celox™, and QuikClot® in control of hemorrhage," Journal of Emergency Medicine, 41(3):237-245.
Dobrovolskaia, MA et al. (Jul.-Aug. 2008) "Preclinical studies to understand nanoparticle interaction with the immune system and its potential effects on nanoparticle biodistribution," Molecular Pharmaceutics, 5(4):487-495.
Duncan, R. (May 2003) "The dawning era of polymer therapeutics," Nature Reviews Drug Discovery, 2(5):347-360.
Finfer, S. et al. (May 2004) "A comparison of albumin and saline for fluid resuscitation in the intensive care unit," New England Journal of Medicine, 350(22):2247-2256.
Fisher-Hoch, SP et al. (Jan. 1989) "Protection of rhesus monkeys from fatal Lassa fever by vaccination with a recombinant vaccinia virus containing the Lassa virus glycoprotein gene," Proceedings of the National Academy of Sciences USA, 86(1):317-321.
Flexner, C et al. (Feb. 1990) "Attenuation and immunogenicity in primates of vaccinia virus recombinants expressing human interleukin-2," Vaccine, 8(1):17-21.
Fries, D. et al, (Aug. 2010) "Role of fibrinogen in trauma-induced coagulopathy," British Journal of Anaesthesia, 105(2):116-121.
Grannis, GF (Jun. 1970) "Plasma fibrinogen: Determination, normal values, physiopathologic shifts, and fluctuations," Clinical Chemistry, 16(6):486-494.
Grünewald, M et al. (Nov. 2002) "Paradoxical hyperfibrinolysis is associated with a more intensely haemorrhagic phenotype in severe congenital haemophilia," Haemophilia, 8(6):768-775.
Gu, B.K. et al. (Aug. 2013) "Fabrication of sonicated chitosan nanofiber mat with enlarged porosity for use as hemostatic materials," Carbohydrate Polymers, 97(1):65-73.
Gustafson, SB et al. (Apr.-Jun. 2007) "Chitosan dressing provides hemostasis in swine femoral arterial injury model," Prehospital Emergency Care, 11(2):172-178.
Guzman, RJ et al. (Dec. 1993) "Efficient and selective adenovirus-mediated gene transfer into vascular neointima," Circulation, 88(6):2838-2848.
Guzman, RJ et al. (Dec. 1993) "Efficient gene transfer into myocardium by direct injection of adenovirus vectors," Circulation Research, 73(6):1202-1207.

* cited by examiner

Hemostatic polymer
Scrambled polymer
Albumin Control
Mean Arterial Pressure (mm Hg)
80
60
40
20
0
5
10
15
20
30
40
50
60
70
Time After Clamp Release (min)

Blood Lactate Concentration (mmol/L)
10
8
6
4
2
0
0
5
10
15
20
30
40
50
60
70
Time After Clamp Release (min)

BIOCOMPATIBLE POLYMERIC SYSTEM FOR TARGETED TREATMENT OF THROMBOTIC AND HEMOSTATIC DISORDERS

This application is a 371 National Phase of PCT/US14/44717 filed Jun. 27, 2014, which claims the benefit of U.S. provisional patent application No. 61/840,310, filed Jun. 27, 2013, the entire contents of which are incorporated herein by reference.

STATEMENT OF GOVERNMENT SUPPORT

This invention was made with government support under UL1 TR000423 and KL2 TR000421, awarded by the National Institutes of Health. The government has certain rights in the invention.

TECHNICAL FIELD OF THE INVENTION

The present invention relates to molecules and methods for treatment of thrombotic and hemostatic disorders. More specifically, the invention relates to biocompatible polymers to which a plurality of clot-modulating peptides are bound. The polymers can be used to present a multivalent display of, for example, fibrin binding peptides that facilitate clot formation. Other agents can be bound to the polymer to weaken clots and achieve other therapeutic benefits.

BACKGROUND OF THE INVENTION

Bleeding is responsible for 30-40% of trauma-associated deaths and is the leading cause of death in the initial 6 hours after injury [Sauaia 1995]. The formation of a strong blood clot is necessary to staunch bleeding. However, blood clots in one-fourth of trauma patients are approximately 40% weaker [Davenport 2011] as a result of disrupted coagulation mechanisms and are therefore susceptible to rebleeding. Large-volume blood loss causes rapid depletion of available clotting factors. In addition, clotting factors are susceptible to dysfunction in the lower pH environment generated from lactic acid production as tissues become reliant on anaerobic respiration to compensate for limited oxygen delivery. Furthermore, hyperfibrinolysis, the accelerated enzymatic breakdown of the clot's supporting matrix, a proteinaceous fibrin fiber network, occurs [Raza 2013]. Reduced clot strength in patients with trauma-induced coagulopathy (TIC) is independently associated to a four-fold increase in 30-day mortality [Brohi 2003, Nystrup 2011].

Hemostasis by formation of a strong clot resistant to fibrinolysis is necessary to reverse coagulopathy and prevent downstream exsanguination and multi-organ failure. Since innate coagulation mechanisms are disabled, current approaches include transfusion of blood components for factor replacement and infusion of antifibrinolytic drugs to prevent clot breakdown. However, these methods have serious associated complications such as multi-organ failure and systemic inflammation and have limited ability to affect the multifactorial pathophysiology of TIC [Moore 1997]. An intravenously-administered hemostatic agent specifically designed to both bolster clot strength and reduce fibrinolysis at inaccessible internal bleeding sites without the aforementioned complications is thus needed. However, there are currently no such injectable hemostatic agents available.

SUMMARY OF THE INVENTION

The invention meets these needs and others by providing a water-soluble polymer to which a plurality of clot-modulating peptides (CMPs) are bound. In one embodiment, the biocompatible polymer comprises repeating units that form a backbone, wherein the repeating units comprise a hydrophilic monomer and a display monomer, and a plurality of pendant clot-modulating peptides (CMPs) bound to the display monomer. Representative examples of a hydrophilic monomer include, but are not limited to, a polycarboxybetaine, polysulfobetaine, polyphosphobetaine, (hydroxyethyl)methacrylate (HEMA), and N-(2-hydroxypropyl) methacrylamide (HPMA). Representative examples of the display monomer include, but are not limited to, those selected from the group consisting of N-hydroxysuccinimidyl ester methacrylate (NHSMA), pyridyl disulfide methacrylamide (PDSMA), N-(3-aminopropyl) methacrylamide hydrochloride (APMA), poly(propylacrylic acid) (PPAA), glycidyl methacrylate, 2-hydroxyethyl methacrylate, methacrylic acid N-hydroxysuccinimide, mono-2-(methacryloyloxy)ethyl maleate, 2-Carboxyethyl acrylate, propargyl acrylate, acrylate-PEG-maleimide, and amino acid-N-carboxyanhydride monomers. In addition, a peptide can serve as a display monomer, as can activated or reactive hydrophilic monomers. For example, HEMA can be used for peptide conjugation. The conjugation provides for multivalent display of CMPs that are pendant at multiple intervals along the length of the polymer.

The repeating units of the polymer can thus form either a homopolymer or a copolymer. The homopolymer contains a subset of units that have been functionalized for peptide display, while the copolymer includes a combination of distinct monomers wherein some are hydrophilic monomers and some are display monomers. One example of a copolymer comprises HEMA as the hydrophilic monomer and N-hydroxysuccinimidyl ester methacrylate (NHSMA), or p(HEMA-co-NHSMA). In a typical embodiment, the repeating units are present at a ratio of 4 hydrophilic monomers to each display monomer (e.g., 80% HEMA and 20% NHSMA).

In other embodiments, the polymer comprises a polycarboxybetaine, polysulfobetaine, polyphosphobetaine, or N-(2-hydroxypropyl)methacrylamide (HPMA) backbone. The CMPs can be bound to the polymer via conjugation to reactive groups on the polymer. For example, the CMPs can be fibrin binding peptides (FBPs) that are conjugated to N-hydroxysuccinimidyl (NHS) reactive groups on the polymer via the ε-amine on the C-terminus lysine.

In a typical embodiment, the CMPs comprise fibrin-binding peptides (FBPs). In some embodiments, the CMPs comprise platelet-binding peptides (PBPs), Von Willebrand Factor binding peptides (VFWBPs), and/or a combination of some or all of FBPs, PBPs, and VFWBPs. In one embodiment, the FBPs are cyclic and the FBPs comprise non-natural amino acids. In a particular embodiment, the FBPs comprise the sequence Ac-Y(DGI)C(HPr)YGLCYIQGK (SEQ ID NO: 1), wherein Ac=acetylation of N-terminus, DGI=D-glutamic acid, HPr=hydroxyproline, cyclized via C3-C8 monodisulfide bond. In another embodiment, the PBPs comprise the amino acid sequence shown in SEQ ID NO: 3.

In one embodiment, the polymer has a degree of polymerization of 100. In a particular embodiment, the polymer has a degree of polymerization of 200. The polymer can have a molecular weight of, for example, about 5 to about 300 kDa, and typically has a molecular weight of 50-60 kDa. In one embodiment, the polymer is a linear polymer. Other embodiments of the polymer include cyclic and branched polymer conformations. In a typical embodiment, the polymer is synthesized by reversible addition-fragmentation chain-transfer (RAFT).

In addition to CMPs, other agents can be bound to the polymer. Examples of agents that can be bound to the polymer include imaging agents, therapeutic agents, and non-peptidic clot-modulating agents. Representative examples of imaging agents include, but are not limited to, imaging agents and therapeutic agents. Representative examples of imaging agents include MR contrast agents (e.g, gadolinium) PET contrast agents or fluorophores Also provided by the invention is a method of accelerating fibrin polymerization in a volume of blood. Typically, the method comprises contacting the volume of blood with a polymer of the invention to which FBPs are bound, whereby cross-linking occurs within and between fibers by the plurality of fibrin-binding peptides during fibrin polymerization. The speed of clot formation can be increased by delivery of agonists, such as thrombin, tissue factor, or specific clotting factor proteins or peptides that are delivered directly to the forming clot as a secondarily attached construct on the polymer. Thus, in some embodiments of the invention, the CMPs bound to the polymer further comprise an agent selected from the group consisting of thrombin, tissue factor, and clotting factors.

Also provided is a method of increasing fibrin stability in a volume of blood, as well as a method of increasing clot strength in a volume of blood. These methods comprise contacting the volume of blood with the polymer of the invention to which FBPs are bound, whereby cross-linking occurs within and between fibers by the plurality of fibrin-binding peptides during fibrin polymerization. The method can further comprise delivery of clot enhancing agents via said polymer. The clot enhancing agents include, for example, platelet binding peptides, activators such as adenosine diphosphate (ADP), collagen, and/or von Willebrand factor binding peptides. Thus, any of the preceding methods can be performed with a polymer that further comprises one or more clot enhancing agents bound thereto, the clot enhancing agents being selected from the group consisting of antifibrinolytic drugs, platelet binding peptides, adenosine diphosphate (ADP), collagen, and von Willebrand factor. The method can also include delivery of specific clot-enhancing peptides, proteins, or drugs delivered to the forming clot that would enhance fibrin stability. Examples of such clot-enhancing agents include antifibrinolytic drugs (epsilon aminocaproic acid (EACA), Tranexamic acid, aprotinin, and plasminogen activator inhibitor 1 (PAI-1))

In addition, the invention provides a method of reducing clot strength in a volume of blood. The method comprises contacting the volume of blood with a synthetic biocompatible polymer, such as a polymer comprising (hydroxyethyl) methacrylate (HEMA), for example, to which a plurality of secondary synthetic polymers are bound. The secondary synthetic polymers disrupt or prevent cross-linking between fibers during fibrin polymerization, thereby reducing clot strength. Reduction of clot strength may be induced directly by structural manipulation of the clot via opening of pore structure, or delivery of anticoagulant or fibrinolytic drugs to the developing clot.

The invention also provides a method of treating a patient suffering from a bleeding disorder. The method comprises administering to the subject a polymer of the invention, as described herein. Also provided is a method of treating a patient suffering from a thrombotic disorder. The method comprising administering to the subject a synthetic biocompatible polymer, such as a polymer comprising (hydroxyethyl)methacrylate (HEMA), to which a plurality of secondary synthetic polymers are bound. The secondary synthetic polymers disrupt or prevent cross-linking between fibers during fibrin polymerization, thereby reducing clot strength in the patient. The bleeding disorder may be acquired or congenital. Examples of congenital bleeding disorders include single factor deficiency (Hemophilia A, B), multiple factor deficiency syndromes, VonWillebrand Disease, hypofibrinogenemia, and congenital platelet syndromes, such as Glanzmann's thrombasthenia. Examples of acquired bleeding disorders include disseminated intravascular coagulation (DIC), acquired hypofibrinogenemia, Trauma-induced coagulopathy, Acquired Factor inhibitor syndromes related to Hemophilia A, B, Acquired platelet dysfunction from drugs (aspirin, ADP inhibitors), idiopathic thrombocytopenic purpura (ITP), and Thrombotic thrombocytopenic purpura (TTP). Reversal agents for drug-induced bleeding from heparin, can include low molecular weight heparin, direct thrombin inhibitors, and/or Factor Xa inhibitors. Thus, in one embodiment, the bleeding disorder is selected from the group consisting of: acquired platelet function defects, congenital platelet function defects, congenital protein C or S deficiency, disseminated intravascular coagulation (DIC), Factor II deficiency, Factor V deficiency, Factor VII deficiency, Factor X deficiency, Factor XII deficiency, Hemophilia A, Hemophilia B, Idiopathic thrombocytopenic purpura (ITP), and Von Willebrand's disease (types I, II, and III).

BRIEF DESCRIPTION OF THE FIGURES

FIG. 1A, a schematic showing the structural hierarchy of fibrin and alteration of individual fibrin fibers and the fibrin network via intra- and interfiber crosslinking by fibrin-binding polymers. Note intra-fiber crosslinks via introduction of polymer crosslinks within and between fibrin protofibrils in upper illustration, and formation of inter-fiber crosslinking between two independently forming fibers in lower illustration; bound polymers with available fibrin-binding domains are possible points of nucleation for fiber formation. FIG. 1B, the hemostatic polymer backbone, a linear copolymer of HEMA and NHSMA synthesized via RAFT polymerization, was grafted with the cyclic fibrin-binding peptide Ac-Y(DGI)C(HPr) YGLCYIQGK-Am (SEQ ID NO: 1) through NHS ester reaction with the lysine ε-amine. A single hemostatic polymer has multiple fibrin-binding domains which enables binding of multiple fibrin monomers, protofibrils, and/or fibers for crosslinking.

FIG. 2A, Confocal images were collected of pure fibrin clots made from a solution of 3 mg/mL fluorescent fibrinogen and 0.167 IU/mL thrombin with PBS or 0.5 μM fluorescent hemostatic polymer or fluorescent scrambled polymer control. Fluorescence from the scrambled polymer control had no distinct morphology. HP fluorescence exhibited fiber morphology which coincided with fibrin signal indicating that the polymer is integrated throughout the fibrin network via binding of hemostatic polymers during fibrin polymerization. Scalebar=10 μm. FIG. 2B, Turbidity of HP-integrated clots (red) was significantly greater than control clots (black) indicating a change in fibrin fiber structure. Increased slopes of turbidity curves also indicated accelerated fibrin formation. FIG. 2C, Permeation studies were used to determine pore sizes in fibrin clots. Flow rates of water through HP-modified clots were severely reduced compared to control clots. Extrapolation of pore sizes using Darcy's Law and a model by Carr and Harding shows significantly reduced pore sizes in HP-modified clots compared to controls. Results are expressed as averages with bars for standard deviation (n=3). Statistical significance was determined using one-way ANOVA with Tukey post hoc test (*p≤0.05). FIG. 2D, SEM imaging confirmed changes in the fibrin network consistent with a highly crosslinked fibrin network. HFXIIIa-treated fibrin was included as a positive control for crosslinking. Altered nanofeatures include smaller pore sizes, presence of thinner fibers, and an overall denser network. Scale bar=250 nm.

FIG. 3A, TEG was used to track the formation and breakdown of pure fibrin clots formed from a solution of 1.5 mg/mL fibrinogen, 0.5 IU/mL thrombin, and 2 μg/mL plasmin with 5 μM HP or controls. TEG traces show the amplitude (i.e. clot strength) over time. HP-modified fibrin clots had traces demonstrating accelerated clot formation, increased clot strength, slowed lysis, and increased clot lifetime (50 min versus 15 min) compared to controls. Quantitative measures such as clotting onset time (R), clotting rate (α-angle), maximum amplitude (MA), and percent of clot lysed 30 min after time to MA (Ly30%) were extracted from TEG traces. FIG. 3B, HP-modified fibrin clots started forming earlier than controls. FIG. 3C, HP-induced crosslinking significantly accelerated fibrin clot formation and FIG. 3D, generated clots significantly stronger than control clots. FIG. 3E, By 30 min after time to MA, control clots were nearly completely lysed while integration of HP into clots significantly reduced Ly30%. Results are expressed as averages with bars for standard deviation (n=3). Statistical significance was determined using one-way ANOVA with Tukey post hoc test (*p≤0.05, *p≤0.001). FIG. 3**F, Application of 10 μg/mL plasmin to the edge of fully-formed fibrin clots and subsequent time-lapsed confocal imaging showed rapid lysis of control clots while HP-modified clots showed dramatically slowed lysis. Scalebar=50 μm.

FIG. 4A, Work flow for evaluating hemostatic polymers in a rat femoral artery injury model. A 3-mm longitudinal incision was made in the isolated femoral artery. Microsurgical clamps were placed proximal and distal to the injury to prevent bleeding. 15 mg/kg polymers were injected, and after 5 min of circulation, rats were normalized to a starting BP of 60 mm Hg via a controlled catheter bleed. Clamps were removed to allow the injury to bleed freely in the first 15 min followed by fluid resuscitation with 0.9% saline to maintain BP above 60 mm Hg, the minimum BP needed for perfusion of vital organs. FIG. 4B, Cumulative hemorrhage volume was significantly reduced in HP-treated rats compared to control groups (n=5). FIG. 4C, HP-treated rats maintained significantly higher blood pressure over time which allowed for better circulation and tissue perfusion as reflected by significantly lower FIG. 4D, circulating lactate levels. FIG. 4E, Due to higher blood pressures in HP-treated rats, significantly lower volumes of saline were needed to maintain BP above 60 mm Hg in HP-treated rats. An albumin control (MW 60 kDa) is included to account for increased oncotic pressures from polymer circulation. Statistical significance was determined using two-way ANOVA with repeated measures and a Tukey post hoc test (*p≤0.05, ***p≤0.001).

FIG. 10. Synergistic effect of hemostatic polymer HP and tranexamic acid (TXA), a clinically-approved antifibrinolytic drug. Fibrin clots were formed with 1.5 mg/mL fibrinogen and 0.5 IU/mL thrombin with the addition of 2 μg/mL plasmin to generate an in vitro hyperfibrinolytic model. TXA alone delays the onset of lysis and increases clot lifetime. Treatment of clots with both TXA and HP increases clotting rate, increases maximum clot strength, and inhibits clot lysis. Lowest (darkest) line is PBS control; second lowest is 2 μg/mL TXA; third lowest is 10 μg/mL TXA; fourth (third from top) is HP; second from top is 2 μg/mL TXA+HP; top line is 10 μg/mL TXA+HP.

DETAILED DESCRIPTION OF THE INVENTION

Figure 1A:
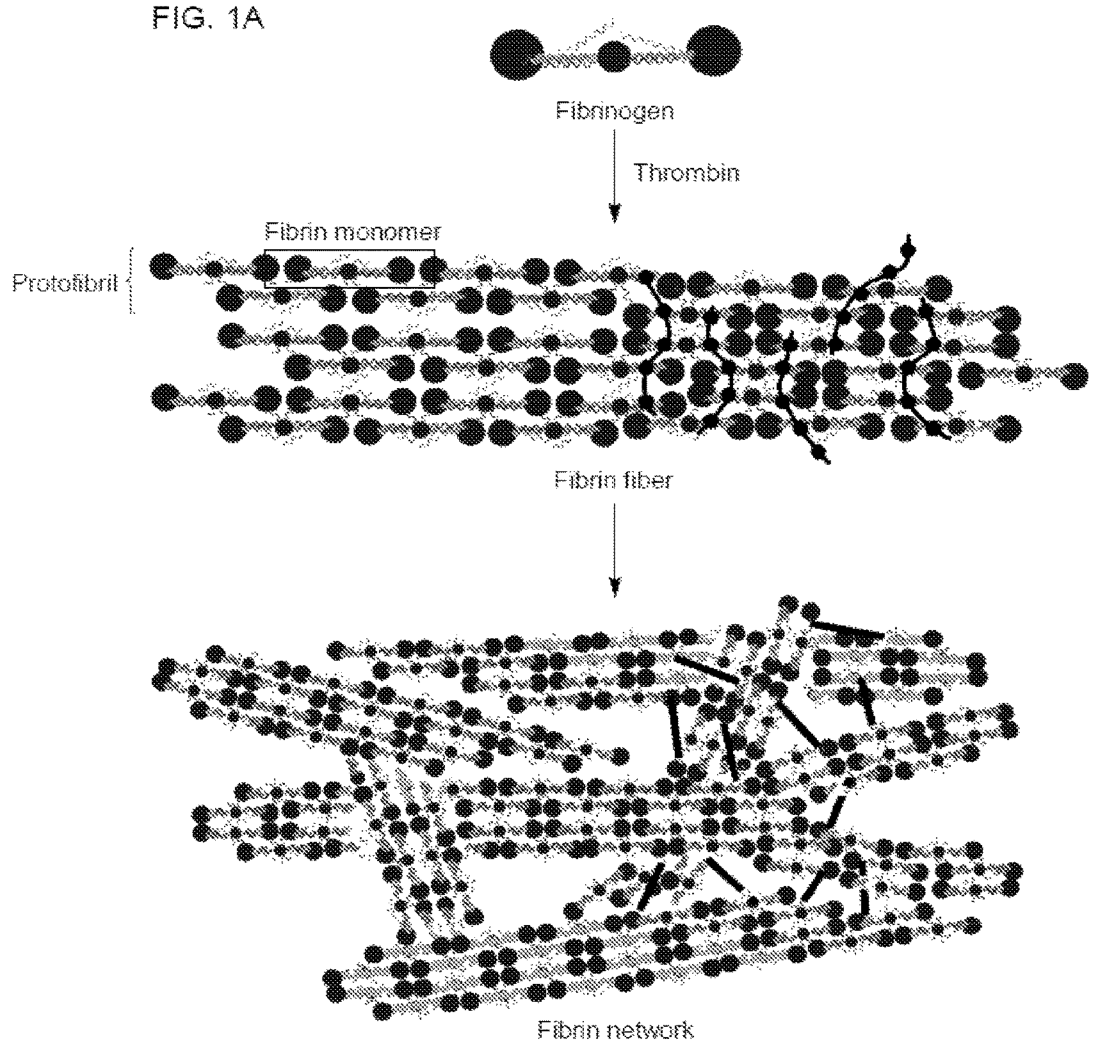
FIGS. 1A-1B. The synthesis of a hemostatic polymer that increases clot strength and resistance to fibrinolysis through fibrin crosslinking.

The present invention is based on the synthesis and evaluation of a hemostatic polymer designed to increase clot strength and prevent fibrinolysis via fibrin fiber crosslinking. The fibrin network is an integral structural component contributing to clot stability. Fibrin is a viscoelastic biopolymer produced by the coagulation cascade locally at the site of vascular injury. Briefly, fibrinogen, a plasma glycoprotein, is cleaved by thrombin to generate fibrin monomers. Fibrin monomers self-polymerize in a half-staggered manner to form protofibrils, which then associate non-covalently, bundle into fibers, and branch to form a three-dimensional hydrogel scaffold for platelets, blood cells, and other clot components.

Crosslinking is used extensively in both man-made and natural hydrogel scaffolds to increase mechanical stability [Hennick 2002]. More generally speaking, crosslinking is a useful process for creating or modifying materials to make them resistant to deformation, chemical degradation, and mechanical failure. Crosslinking is thus a promising solution for weakened blood clots, which must withstand both shear stress from blood flow as well as enzymatic degradation to prevent blood loss. An example of particular relevance is fibrin crosslinking by the naturally-occurring transglutaminase Factor XIIIa (FXIIIa). FXIIIa creates inter- and intra-fiber crosslinks by forming isopeptide bonds between lysines and glutamic acid residues, and this crosslinking has been shown to increase shear moduli of clots (a measure of clot stiffness) and resistance to fibrinolysis [Theusinger 2010, Hethershaw 2014]. FXIIIa-treated fibrin clots have thinner fiber diameters, greater fiber density, and smaller pores for a given fibrinogen concentration. Therefore, the fibrin-cleaving enzyme plasmin has a greater number of fibers to cleave before complete degradation of clots, and smaller pores provide a diffusional barrier for plasmin to infiltrate the clot. Thus, crosslinking fibrin can serve to strengthen clot structure and function.

The polymers of the invention can be used to modulate clotting in a variety of ways via multivalent display of fibrin-binding peptides and other clot-binding and clot-modulating moieties on polymer or co-polymer backbones. In addition to clot-modulating moieties, imaging agents and therapeutic agents can be conjugated to the polymers to facilitate imaging of blood flow and thrombosis, and for treatment of clotting-related disorders.

DEFINITIONS

All scientific and technical terms used in this application have meanings commonly used in the art unless otherwise specified. As used in this application, the following words or phrases have the meanings specified.

As used herein, "peptide" or "polypeptide" includes fragments of proteins, and peptides, including aptamers, whether isolated from natural sources, produced by recombinant techniques or chemically synthesized. Polypeptides (and peptides) of the invention typically comprise at least 2, more typically, at least about 6 amino acids. In some embodiments, the polypeptides are at least about 12 amino acids in length.

As used herein, a "derivative" of a polypeptide or polynucleotide refers to a molecule having one, some or all amino acids or nucleic acids in the indicated sequence substituted with a non-natural derivative of the indicated amino acid or nucleic acid.

As used herein, a "fibrin binding peptide" means a peptide that binds fibrin with a higher affinity than it binds to other targets (unrelated to fibrin).

As used herein, a "biocompatible polymer" means a polymer that is suitable for contact with bodily tissues and fluids because it does not cause an allergic reaction or other significant adverse side effects within a relevant dose range.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, a "heterologous molecule" is not identical to the reference molecule, nor is it, in the context of polypeptides and polynucleotides, an adjacent native sequence with respect to the reference molecule. Heterologous molecules are not limited to polypeptides and polynucleotides.

As used herein, "small molecule" refers to a low molecular weight organic compound having a molecular weight of less than 2000 Daltons, in some embodiments less than 1000 Daltons, and in still other embodiments less than 500 Daltons or less. A small molecule is typically between about 300 and about 700 Daltons. In a typical embodiment, a small molecule for use with the invention binds with high affinity to a protein, nucleic acid molecule, or a polysaccharide and alters the activity or function of the biopolymer to which it binds. Such molecules include, for example, heterocyclic compounds, carboxylic compounds, sterols, amino acids, lipids, and nucleic acids.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, a "delivery vehicle" or "carrier" means an element capable of carrying any type of cargo, such as small molecules, imaging agents, proteins, peptides, etc. For example, a delivery vehicle can be a polymer, nanoparticle or peptide carrier, and used for drugs or other cargo, and that can be attached to the biocompatible polymer of the invention for delivery.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

The term "antibody" is used in the broadest sense and specifically covers single monoclonal antibodies and antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well-known conventional methods (see, for example, *Remington's Pharmaceutical Sciences,* 18th edition, A. Gennaro, ed., Mack Publishing Co., Easton, Pa., 1990).

As used herein, "a" or "an" means at least one, unless clearly indicated otherwise.

Biocompatible Polymers for Multivalent Display

Biocompatible polymers are suitable for contact with bodily fluids and tissues, and thus for administration to the body, e.g., via injection. Suitable polymers will not cause cytotoxicity, chronic inflammation, or other adverse effects. In one embodiment, the polymer is water-soluble. Biocompatibility can be tested using techniques known in the art, such as by following ISO 10993 series.

Biocompatible polymers, as described herein, may be of any length between about 8 to about 2000 units (monomers) in length, and may be between 50 and 300 units, or more typically, between 20 and 500 units in length. Preferably, the polymer is produced by controlled polymerization. In one embodiment, the polymer has a degree of polymerization of 100. In a particular embodiment, the polymer has a degree of polymerization of 200. The polymer typically has a molecular weight of 50-60 kDa, but can be between about 5 and about 300 kDa, or between 20 and 200 kDa, depending on the monomers employed. In one embodiment, the polymer is a linear polymer. Other embodiments of the polymer include cyclic and branched polymer conformations, including star and sunflower conformations. In one embodiment, the polymer is synthesized by living polymerization techniques such as reversible addition-fragmentation chain transfer (RAFT) or Atom transfer radical polymerization (ATRP). Other methods of polymer synthesis that are known in the art may be employed.

The invention provides a biocompatible polymer to which a plurality of clot-modulating peptides (CMPs) are bound. In one embodiment, the polymer comprises (hydroxyethyl) methacrylate (HEMA). Optionally, the polymer further comprises N-hydroxysuccinimidyl ester methacrylate (NHSMA), wherein the NHSMA is present as a co-polymer with HEMA (p(HEMA-co-NHSMA)). In one embodiment, the co-polymer is about 80% HEMA and about 20% NHSMA. In other embodiments, the polymer comprises a zwitterion (e.g., polycarboxybetaine, polysulfobetaine, polyphosphobetaine; see PCT/US2008/084095, PCT/US2006/028988, PCT/US2007/075409), or N-(2-hydroxypropyl)methacrylamide (HPMA) backbone.

Examples of hydrophilic monomers suitable for use as described herein include N-(3-aminopropyl)methacrylamide (APMA), N, N-diethylacrylamide, N-[3-(Dimethylamino)propyl]methacrylamide, N-hydroxyethyl acrylamide, 2-aminoethyl methacrylate, 2-(Dimethylamino)ethyl methacrylate, 2-ethoxyethyl methacrylate, Ethylene glycol methyl ether methacrylate, Ethyl methacrylate, Glycidyl methacrylate, Glycosyloxyethyl methacrylate and other carbohydrate methacrylates, acrylates, methacrylamides, or methacrylates; 2-hydroxyethyl methacrylate, Hydroxypropyl methacrylate, Poly(ethylene glycol) methacrylate, Propyl methacrylate, 3-sulfopropyl methacrylate, Triethylene glycol methyl ether methacrylate, 2-(diethylamino)ethyl acrylate, 2-(dimethylamino)propyl acrylate, Di(ethylene glycol)2-ethylhexyl ether acrylate, Ethyl-2-ethylacrylate, 2-hydroxyethyl acrylate, Poly(ethylene glycol) methyl ether acrylate, 24-hydroxybutyl acrylate, and Aminoacid-N-carboxyanhydride monomers. Additional examples of hydrophilic monomers include N-acryloylamido-ethoxyethanol, N-isopropylacrylamide, N-isopropylmethacrylamide, methacrylamide, 2-acrylamido-2-methyl-1-propanesulfonic acid, N-Tris(hydroxymethyl)methyl]acrylamide, Methyl methacrylate, 2-N-morpholinoethyl methacrylate, 2-(2-oxo-1-imidazolidinyl)ethyl methacrylate, and 3-sulfopropyl acrylate.

The CMPs can be bound to the polymer via conjugation to reactive groups on the polymer. For example, the CMPs can be fibrin binding peptides (FBPs) that are conjugated to N-hydroxysuccinimidyl (NHS) reactive groups on the polymer via the ε-amine on the C-terminus lysine. Other examples of conjugation chemistry that can be employed for binding CMPs to the polymer include, but are not limited to, azide-alkyne coupling chemistry, thiol-ene chemistries, thiol-disulfide exchange, and hydrazone bond chemistry. In addition, a peptide can serve as a display monomer, as can activated or reactive hydrophilic monomers. For example, HEMA can be used for peptide conjugation. The conjugation provides for multivalent display of CMPs that are pendant at multiple intervals along the length of the polymer.

Examples of reactive monomers include pyridyl disulfide methacrylamide, glycidyl methacrylate, 2-hydroxyethyl methacrylate, methacrylic acid N-hydroxysuccinimide, mono-2-(methacryloyloxy)ethyl maleate, 2-Carboxyethyl acrylate, propargyl acrylate (or protected form), acrylate-PEG-maleimide, amino acid-N-carboxyanhydride monomers, alkyne monomers, and maleimide monomers.

In addition to CMPs, other agents can be bound to the polymer. Examples of agents that can be bound to the polymer include imaging agents, therapeutic agents, and non-peptide clot-modulating agents. Representative examples of imaging agents include, but are not limited to, MR contrast agents (e.g, gadolinium), positron emission tomography (PET) contrast agents, or fluorophores.

Clot-Modulating Peptides & Nucleic Acids

The polymers of the invention feature a plurality of moieties conjugated thereto. In some embodiments, the moieties are clot-modulating peptides (CMPs), such as fibrin binding peptide (FBP) or other clot-binding peptides (CBPs). In some embodiments, the clot modulation is performed by aptamers, including both peptide and nucleic acid aptamers, which can be conjugated to the polymer and serve the same function. CMPs can facilitate clot formation, or, in some embodiments, CMPs are deployed to weaken clot structure, e.g., by introducing synthetic polymers into the fibrin network, such as for treatment of thrombotic disease. Additional moieties that could be bound to the polymers include imaging agents and therapeutic agents. Representative examples of imaging agents that can be used include MR contrast agents (e.g, gadolinium) PET contrast agents or fluorophores.

Clot-modulating peptides influence clots by either enhancing their development or stability, or by weakening clot formations. In a typical embodiment, the CMPs to be bound to polymers of the invention comprise fibrin-binding peptides (FBPs). In some embodiments, the CMPs further comprise platelet-binding peptides. In one embodiment, the FBPs are cyclic and the FBPs comprise non-natural amino acids. In a particular embodiment, the FBPs comprise the sequence Ac-Y(DGI)C(HPr)YGLCYIQGK (SEQ ID NO: 1), wherein Ac=acetylation of N-terminus, DGI=D-glutamic acid, HPr=hydroxyproline, cyclized via C3-C8 monodisulfide bond. Other fibrin binding peptides are known in the art. See, e.g., U.S. Pat. Nos. 6,991,775, 7,238,341, and 8,466, 107, as well as Kolodziej, 2012, Bioconj. Chem. 23:548-556; Overoye-Chan, 2009, J. Am. Chem. Soc. 130:6025-6039; and Vymazal, 2009, Invest. Radiol. 44:697-704.

TABLE 1

| Representative Peptide Sequences: | | |
|---|---|---|
| Name | Amino Acid Sequence | SEQ ID NO: |
| FBP-X | Ac-Y(DGI)C(HPr)YGLCYIQGK | 1 |
| Scrambled FBP | Ac-YICGQ(DGI)AC(HPr)LYGK | 2 |
| Platelet binding peptide | HHLGGAKQAGDV | 3 |

Cyclic peptide structures can be constructed for use in the invention. Representative approaches for cyclizing peptides include: use of flanking cysteines that form disulfide bonds, terminus cyclization or lactam bridges. Peptides may be N- or C-terminus modified to enhance peptide stability. Peptides are typically synthesized using solid phase or solution phase synthesis.

In some embodiments, the peptide comprises D-amino acids, β-amino acids, other non-natural amino acids, and/or has been structurally modified to enhance its utility for a given purpose. In some embodiments, the peptide comprises chemically modified amino acids.

Those skilled in the art will appreciate that certain variants thereof will be useful in the methods of the invention. A peptide "variant," as used herein, is a peptide that differs from a native peptide in one or more substitutions, deletions, additions and/or insertions, such that the clot-modulating activity of the peptide is not substantially diminished. In other words, the ability of a variant to modulate clotting may be enhanced or unchanged, relative to the native peptide, or may be diminished by less than 50%, and preferably less than 20%, relative to the native peptide. Such variants may generally be identified by modifying one of the above peptide sequences and evaluating the activity of the modified peptide using assays as described herein. Peptide variants preferably exhibit at least about 85%, more preferably at least about 90% and most preferably at least about 95% identity (determined as described above) to the identified peptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the peptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant peptides differ from a native sequence by substitution, deletion or addition of five amino acids or fewer.

Recombinant peptides encoded by DNA sequences as described herein may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant peptide. Suitable host cells include prokaryotes, yeast and higher eukaryotic cells. Preferably, the host cells employed are *E. coli*, yeast, insect cells or a mammalian cell line such as COS or CHO. Supernatants from suitable host/vector systems that secrete recombinant protein or peptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant peptide.

Portions and other variants having fewer than about 50 amino acids may also be generated by synthetic means, using techniques well known to those of ordinary skill in the art. In some embodiments, polypeptides of 6-50 amino acids in length are preferred, with lengths of 10-20 amino acids particularly suited to some uses. Such peptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of peptides is commercially available from suppliers such as Perkin Elmer/Applied BioSystems Division (Foster City, Calif.), and may be operated according to the manufacturer's instructions.

Peptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture:trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

In general, peptides (including fusion proteins) and polynucleotides as described herein are isolated. An "isolated" peptide or polynucleotide is one that is removed from its original environment. For example, a naturally occurring protein is isolated if it is separated from some or all of the coexisting materials in the natural system. Preferably, such peptides are at least about 90% pure, more preferably at least about 95% pure and most preferably at least about 99% pure. A polynucleotide is considered to be isolated if, for example, it is cloned into a vector that is not a part of the natural environment.

Polynucleotides that encode one or more clot-modulating peptides may be employed. Preferred polynucleotides comprise at least 15 consecutive nucleotides, preferably at least 30 consecutive nucleotides and more preferably 35 consecutive nucleotides that encode a CMP. Polynucleotides that are fully complementary to any such sequences are also encompassed by the present invention. Polynucleotides may be single-stranded (coding or antisense) or double-stranded, and may be DNA or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., a sequence that encodes a CMP as described above or a portion thereof) or may comprise a variant of such a sequence, or an aptamer. Polynucleotide variants contain one or more substitutions, additions, deletions and/or insertions such that activity (including clot modulation or specific binding, as appropriate) of the encoded peptide is not diminished, relative to a native peptide. Variants preferably exhibit at least about 60% identity, more preferably at least about 80% identity and most preferably at least about 90% identity to a polynucleotide sequence that encodes a native peptide or a portion thereof.

Two polynucleotide or peptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or peptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native protein (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a peptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art, including, for example, oligonucleotide synthesis. Libraries can be screened with probes designed to identify the gene of interest or the peptide encoded by it. Screening the cDNA or other library with the selected probe may be conducted using standard procedures, such as those described in Sambrook et al., *Molecular Cloning: A Laboratory Manual* (New York: Cold Spring Harbor Laboratory Press, 1989).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}P$-labeled ATP, biotinylation or enzyme labeling. Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a CMP, or portion thereof, provided that the DNA is incorporated into a vector with a suitable RNA polymerase promoter (such as T7 or SP6). Certain portions may be used to prepare an encoded peptide, as described herein.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine. Aptamers, oligonucleotides that recognize and bind to specific protein surfaces and therefore can interfere with the protein activity of a target, are typically modified for therapeutic use. Where rapid clearance is desired, however, non-modified aptamers can be used in methods of the invention.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art. Some embodiments of the peptides of the invention have been described herein with a cell penetrating peptide (CPP) incorporated into the peptide for facilitation of entry into a cell.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Pharmaceutical Compositions

The invention provides CMPs, peptidomimetics, and/or polynucleotides that are incorporated into pharmaceutical compositions. One example of a polynucleotide that can be employed is a nucleic acid aptamer that can be substituted for a CMP as described herein, achieving a similar objective as a peptide aptamer. Pharmaceutical compositions comprise one or more such compounds and, optionally, a physiologically acceptable carrier. Pharmaceutical compositions within the scope of the present invention may contain other compounds that may be biologically active or inactive. For example, one or more portions of other biologically active molecules may be present, either incorporated into a fusion polypeptide or as a separate compound, within the composition.

A pharmaceutical composition can contain DNA encoding one or more of the peptides as described above, such that the peptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N. Y. Acad Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the delivered molecule. Such excipients are those substances usually and customarily employed to formulate dosages for parenteral administration in either unit dose or multi-dose form or for direct infusion into the CSF by continuous or periodic infusion from an implanted pump.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

The compositions described herein may be administered as part of a sustained release formulation (i.e., a formulation such as a capsule or sponge that effects a slow release of compound following administration, or other implantable device). Such formulations may generally be prepared using well known technology and administered by, for example, oral, rectal or subcutaneous implantation, or by implantation at the desired target site, such as within a muscle. Sustained-release formulations may contain a peptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Methods of Clot Modulation

The invention provides methods of using the biocompatible polymers described herein, for example, in a method of accelerating fibrin polymerization in a volume of blood. Typically, the method comprises contacting the volume of blood with a polymer of the invention to which FBPs are bound, whereby cross-linking occurs within and between fibers by the plurality of fibrin-binding peptides during fibrin polymerization. The speed of clot formation can be increased by delivery of agonists, such as thrombin, tissue factor, or specific clotting factor proteins or peptides that are delivered directly to the forming clot as a secondarily attached construct on the polymer. Thus, in some embodiments of the invention, the CMPs bound to the polymer further comprise an agent selected from the group consisting of thrombin, tissue factor, and clotting factors.

Also provided is a method of increasing fibrin stability in a volume of blood, as well as a method of increasing clot strength in a volume of blood. These methods comprise contacting the volume of blood with the polymer of the invention to which FBPs are bound, whereby cross-linking occurs within and between fibers by the plurality of fibrin-binding peptides during fibrin polymerization. The method can further comprise delivery of clot enhancing agents via said polymer. The clot enhancing agents include, for example, platelet binding peptides, activators such as adenosine diphosphate (ADP), collagen, and/or von Willebrand factor binding peptides. Thus, any of the preceding methods can be performed with a polymer that further comprises one or more clot enhancing agents bound thereto, the clot enhancing agents being selected from the group consisting of antifibrinolytic drugs, platelet binding peptides, adenosine diphosphate (ADP), collagen, and von Willebrand factor. The method can also include delivery of specific clot-enhancing peptides, proteins, or drugs delivered to the forming clot that would enhance fibrin stability. Examples of such clot-enhancing agents include antifibrinolytic drugs (epsilon aminocaproic acid (EACA), Tranexamic acid, aprotinin, and plasminogen activator inhibitor 1 (PAI-1))

In addition, the invention provides a method of reducing clot strength in a volume of blood. The method comprises contacting the volume of blood with a synthetic biocompatible polymer as described herein, such as a polymer comprising (hydroxyethyl)methacrylate (HEMA), for example, to which a plurality of secondary synthetic polymers are bound. The secondary synthetic polymers disrupt or prevent cross-linking between fibers during fibrin polymerization, thereby reducing clot strength. Reduction of clot strength may be induced directly by structural manipulation of the clot via opening of pore structure, or delivery of anticoagulant or fibrinolytic drugs to the developing clot.

The invention also provides a method of treating a patient suffering from a bleeding disorder. The method comprises administering to the subject a polymer of the invention, as described herein. Also provided is a method of treating a patient suffering from a thrombotic disorder. The method comprising administering to the subject a synthetic biocompatible polymer as described herein, such as a polymer comprising (hydroxyethyl)methacrylate (HEMA), to which a plurality of secondary synthetic polymers are bound. The secondary synthetic polymers disrupt or prevent cross-linking between fibers during fibrin polymerization, thereby reducing clot strength in the patient.

Therapeutic and Prophylactic Methods

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

Peptides or nucleic acid based drugs (e.g., antisense RNAs, siRNAs, mRNAs) can be delivered to cells via chemical means, biological means, carrier peptides, vectors, or physical delivery systems. Representative chemical means include, but are not limited to, specific chemical substances, including cationic polymers such as polyethylenimine (PEI) and cationic lipids. An example of a biological means of delivery is cell-penetrating peptides (CPPs). An exemplary carrier peptide is transportan. Vectors include plasmids and viruses, or cells. Representative physical delivery systems include, but are not limited to electrically-based systems and those using mechanical force, such as gene guns.

Conditions to be treated include, but are not limited to, a hemostatic or thrombotic disease. The hemostatic disorder, or bleeding disorder, may be acquired or congenital. Examples of congenital bleeding disorders include single factor deficiency (Hemophilia A, B), multiple factor deficiency syndromes, VonWillebrand Disease, hypofibrinogenemia, and congenital platelet syndromes, such as Glanzmann's thrombasthenia. Examples of acquired bleeding disorders include disseminated intravascular coagulation (DIC), acquired hypofibrinogenemia, Trauma-induced coagulopathy, Acquired Factor inhibitor syndromes related to Hemophilia A, B, Acquired platelet dysfunction from drugs (aspirin, ADP inhibitors), idiopathic thrombocytopenic purpura (ITP), and Thrombotic thrombocytopenic purpura (TTP). Reversal agents for drug-induced bleeding from heparin, can include low molecular weight heparin, direct thrombin inhibitors, and/or Factor Xa inhibitors. Thus, in one embodiment, the bleeding disorder is selected from the group consisting of: acquired platelet function defects, congenital platelet function defects, congenital protein C or S deficiency, disseminated intravascular coagulation (DIC), Factor II deficiency, Factor V deficiency, Factor VII deficiency, Factor X deficiency, Factor XII deficiency, Hemophilia A, Hemophilia B, Idiopathic thrombocytopenic purpura (ITP), and Von Willebrand's disease (types I, II, and III).

Administration and Dosage

The compositions are administered in any suitable manner, optionally as pharmaceutically acceptable salts or with pharmaceutically acceptable carriers. Suitable methods of administering compositions, moieties, and molecules in the context of the present invention to a subject are available, and, although more than one route can be used to administer a composition, a particular route can often provide a more immediate and more effective reaction than another route.

The dose administered to a patient, in the context of the present invention, should be sufficient to effect a beneficial therapeutic response in the patient over time, to delay onset of disease, or to inhibit disease progression. Thus, the composition is administered to a subject in an amount sufficient to alleviate, reduce, and cure or at least partially delay or arrest symptoms and/or complications from the disease. An amount adequate to accomplish this is defined as a "therapeutically effective dose."

A suitable dose is an amount that, when administered as described herein, is capable of promoting a reduction in symptoms, and preferably at least 10-50% improvement over the basal (i.e., untreated) level. Such therapies should lead to an improved clinical outcome (e.g., more frequent remissions, complete or partial or longer disease-free survival) in patients as compared to untreated patients. In general, for pharmaceutical compositions comprising one or more peptides, the amount of each peptide present in a dose ranges from about 100 μg to 5 mg per kg of host. Suitable volumes will vary with the size of the patient, but will typically range from about 0.1 mL to about 5 mL.

Routes and frequency of administration of the therapeutic compositions disclosed herein, as well as dosage, will vary from individual to individual, and may be readily established using standard techniques. In general, the pharmaceutical compositions may be administered, by injection or implantation (e.g., intracutaneous, intratumoral, intramuscular, intraperitoneal, intravenous, intrathecal, epidural or subcutaneous), intranasally (e.g., by aspiration) or orally. Typically the administration is intravenous. In one example, between 1 and 10 doses may be administered over a 52 week period. Preferably, 6 doses are administered, at intervals of 1 month, and booster administrations may be given periodically thereafter, as indicated. Alternate protocols may be appropriate for individual patients. In one embodiment, 2 intradermal injections of the composition are administered 10 days apart. In another embodiment, a dose is administered daily or once every 2 or 3 days over an extended period, such as weeks or months.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients.

Kits

For use in the methods described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a biocompatible polymer that is, optionally, detectably labeled. The polymer has CMPs bound thereto, as described herein, or polynucleotides encoding CMPs, or peptide or nucleic acid aptamers, in accordance with the invention. Optionally, included in the same or a separate container, the kit comprises a CMP attached or to be attached to the polymer. The kit can also include one or more containers for a reporter-means, such as a biotin-binding protein, e.g., avidin or streptavidin, bound to a detectable label, e.g., an enzymatic, florescent, or radioisotope label for use in monitoring the polymer. The kit can include all or part of an amino acid sequence described herein, or a nucleic acid molecule that encodes such amino acid sequences.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described above. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1: Fibrin-Crosslinking Polymers for Modulating Clot Properties and Inducing Hemostasis This example demonstrates a linear (hydroxyethyl)methacrylate (HEMA)-based hemostatic polymer (HP) with multivalent display of fibrin-binding domains designed to crosslink the fibrin matrix in blood clots to increase clot strength and simultaneously integrate synthetic HEMA polymers into fibrin fibers during clot formation to create a fortified hybrid polymer network resistant to enzymatic degradation. Specificity of binding domains to fibrin allows the polymer to hone in to sites of vascular injury after intravascular administration and subsequently crosslink blood clots in situ. In a rat femoral artery injury model, hemorrhage volumes and resuscitative infusion volumes to maintain blood pressure at 60 mm Hg were significantly reduced in HP-treated rats suggesting an increased hemostatic ability. Our findings demonstrate that introduction of synthetic polymer crosslinks to the fibrin matrix of blood clots is a viable method of modulating clot strength and resistance to fibrinolysis.

Bleeding is responsible for 30-40% of trauma-associated deaths and is the leading cause of death in the initial 6 hours after injury [Sauaia 1995]. The formation of a strong blood clot is necessary to staunch bleeding. However, blood clots in one-fourth of trauma patients are approximately 40% weaker [Davenport 2011] as a result of disrupted coagulation mechanisms and are therefore susceptible to rebleeding. Large-volume blood loss causes rapid depletion of available clotting factors. In addition, clotting factors are susceptible to dysfunction in the lower pH environment generated from lactic acid production as tissues become reliant on anaerobic respiration to compensate for limited oxygen delivery. Furthermore, hyperfibrinolysis, the accelerated enzymatic breakdown of the clot's supporting matrix, a proteinaceous fibrin fiber network, occurs [Raza 2013]. Reduced clot strength in patients with trauma-induced coagulopathy (TIC) is independently associated to a four-fold increase in 30-day mortality [Brohi 2003, Nystrup 2011].

Hemostasis by formation of a strong clot resistant to fibrinolysis is necessary to reverse coagulopathy and prevent downstream exsanguination and multi-organ failure. Since innate coagulation mechanisms are disabled, current approaches include transfusion of blood components for factor replacement and infusion of antifibrinolytic drugs to prevent clot breakdown. However, these methods have serious associated complications such as multi-organ failure and systemic inflammation and have limited ability to affect the multifactorial pathophysiology of TIC [Moore 1997]. An intravenously-administered hemostatic agent specifically designed to both bolster clot strength and reduce fibrinolysis at inaccessible internal bleeding sites without the aforementioned complications is thus needed. However, there are currently no such injectable hemostatic agents available.

This example describes the synthesis and evaluation of a hemostatic polymer designed to increase clot strength and prevent fibrinolysis via fibrin fiber crosslinking. As previously mentioned, the fibrin network is an integral structural component contributing to clot stability [Lord 2007]. Fibrin is a viscoelastic biopolymer produced by the coagulation cascade locally at the site of vascular injury. Briefly, fibrinogen, a plasma glycoprotein, is cleaved by thrombin to generate fibrin monomers. Fibrin monomers self-polymerize in a half-staggered manner to form protofibrils which then associate non-covalently, bundle into fibers, and branch to form a three-dimensional hydrogel scaffold for platelets, blood cells, and other clot components.

Crosslinking is used extensively in both man-made and natural hydrogel scaffolds to increase mechanical stability [Hennick 2002]. More generally speaking, crosslinking is a useful process for creating or modifying materials to make them resistant to deformation, chemical degradation, and mechanical failure. Crosslinking is thus a promising solution for weakened blood clots which must withstand both shear stress from blood flow as well as enzymatic degradation to prevent blood loss. An example of particular relevance is fibrin crosslinking by the naturally-occurring transglutaminase Factor XIIIa (FXIIIa). FXIIIa creates inter- and intra-fiber crosslinks by forming isopeptide bonds between lysines and glutamic acid residues, and this crosslinking has been shown to increase shear moduli of clots (a measure of clot stiffness) and resistance to fibrinolysis [Theusinger 2010, Hethershaw 2014]. FXIIIa-treated fibrin clots have thinner fiber diameters, greater fiber density, and smaller pores for a given fibrinogen concentration. Therefore, the fibrin-cleaving enzyme plasmin has a greater number of fibers to cleave before complete degradation of clots, and smaller pores provide a diffusional barrier for plasmin to infiltrate the clot. Thus, there is strong precedence for crosslinking fibrin to strengthen clot structure and function.

Fibrin-Crosslinking Hemostatic Polymer Design

Deviating from traditional chemical crosslinking methods, we endeavored to introduce synthetic polymer crosslinks within and between fibrin fibers via multivalent binding of fibrin-binding domains grafted on a linear polymer backbone (FIG. 1A). This method allows us to simultaneously crosslink fibrin to increase clot stiffness and integrate synthetic polymers resistant to plasmin degradation into fibers during fibrin polymerization to create a fortified hybrid polymer network. Thus, this hemostatic polymer is designed to increase resistance to both mechanical and chemical degradation and address the multifactorial nature of trauma-induced coagulopathy. To achieve this crosslinking in situ, hemostatic polymers needed to demonstrate high specificity for fibrin. Incorporation of multiple fibrin-binding domains gives the polymer the ability to hone in to sites of vascular injury after intravenous administration, enhances affinity of the polymer to fibrin due to avidity effects, and enables fibrin crosslinking. A fibrin-specific peptide previously isolated by Kolodziej et al. [Kolodziej 2012] using phage display was identified as a suitable fibrin-binding domain for multiple reasons. The peptide is cyclic and was altered with non-natural amino acids, making it more resistant to protease and peptidase activity while in circulation. Binding of this peptide to fibrin is conserved across multiple species including humans, pigs, and rats [Overoye-Chan 2008] and is therefore opportune for evaluation in animal injury models and subsequent clinical translation. Finally, it has been validated and previously shown to accumulate in fibrin-rich thrombi in humans [Vymazal 2009]. A glycine spacer was added to the C-terminus and lysine for conjugation to the polymer backbone.

Advances in living polymerization techniques have facilitated synthesis of polymers that are monodisperse, reproducible, and easily scaled for production making them suited for biomedical applications. A linear polymer with a targeted composition of 80% (hydroxyethyl)methacrylate (HEMA) and 20% N-hydroxysuccinimidyl ester methacrylate (NHSMA), p(HEMA-co-NHSMA), was synthesized by reversible addition-fragmentation chain-transfer (RAFT) for the hemostatic polymer backbone. Poly(HEMA) are FDA-approved, biocompatible polymers previously used in hydrogel implants for a myriad of applications [ref] and was therefore a suitable starting material for hemostatic polymers. The polymer backbone functions as a scaffold for the multivalent display of fibrin-specific peptides, and its molecular weight can be altered to tune pharmacokinetic properties. p(HEMA-co-NHSMA) with a degree of polymerization (DP) of 200 was used for a final product with molecular weight nearing the upper end of the renal threshold (~50-60 kDa) to prevent rapid clearance after intravenous administration.

Figure 1B:
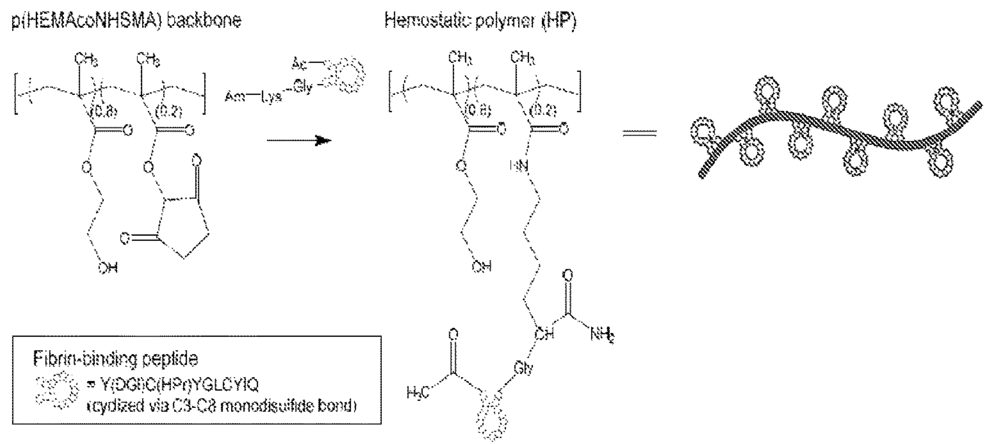

Synthesis of hemostatic polymers (HP) was completed by grafting peptides to the HEMA-based polymer backbone (FIG. 1B). Peptides were conjugated via the ε-amine in the lysine side-chain to NHS esters on the polymer backbone. Conjugation efficiency was approximately 40% (16 peptides per polymer). A scrambled polymer control (SCRP) was synthesized by grafting peptide with a scrambled fibrin-specific sequence to the same polymer backbone. Monomer composition, molecular weight, and polydispersity of HP, its precursors, and SCRP were characterized using $H^1$ NMR, GPC, and UV absorbance (Table 2).

TABLE 2

Properties of hemostatic polymers, precursors, and controls.

| Polymer | Theoretical MW | Actual MW[a] | PDI[b] | Peptides per polymer[c] |
|---|---|---|---|---|
| p($HEMA_{160}$-co-$NHSMA_{40}$) | $2.815 \times 10^4$ | $2.948 \times 10^4$ | 1.432 | NA |
| HEMA backbone[d] | NA | $3.405 \times 10^4$ | 1.239 | NA |
| HP | NA | $4.454 \times 10^4$ | 1.237 | 16 |
| SCRP | NA | $4.660 \times 10^4$ | 1.421 | 16 |
| p($HEMA_{156}$-co-$NHSMA_{40}$-co-$FMA_4$) | $2.923 \times 10^4$ | $2.558 \times 10^4$ | 1.236 | NA |
| fHP | NA | | | 14 |
| fSCRP | NA | | | |

[a,b]Polymers were dissolved in DMF at 5 mg/mL and GPC was used to measure molecular weights and PDIs.
[c]HP and SCRP were dissolved at 5 mg/mL in PBS, and absorbance at 280 nm was measured using a Nanodrop to quantify the number of peptides per polymer.
[d]HEMA backbone is generated by placing p($HEMA_{160}$-co-$NHSMA_{40}$) under the same conjugation reaction and purification conditions as HP and SCRP in the absence of peptide. NHS groups are reacted with 1-amino-2-propanol or hydrolyzed in the process.

Hemostatic Polymer Integration and Alteration of Fibrin Clot Structure

Figure 2A:
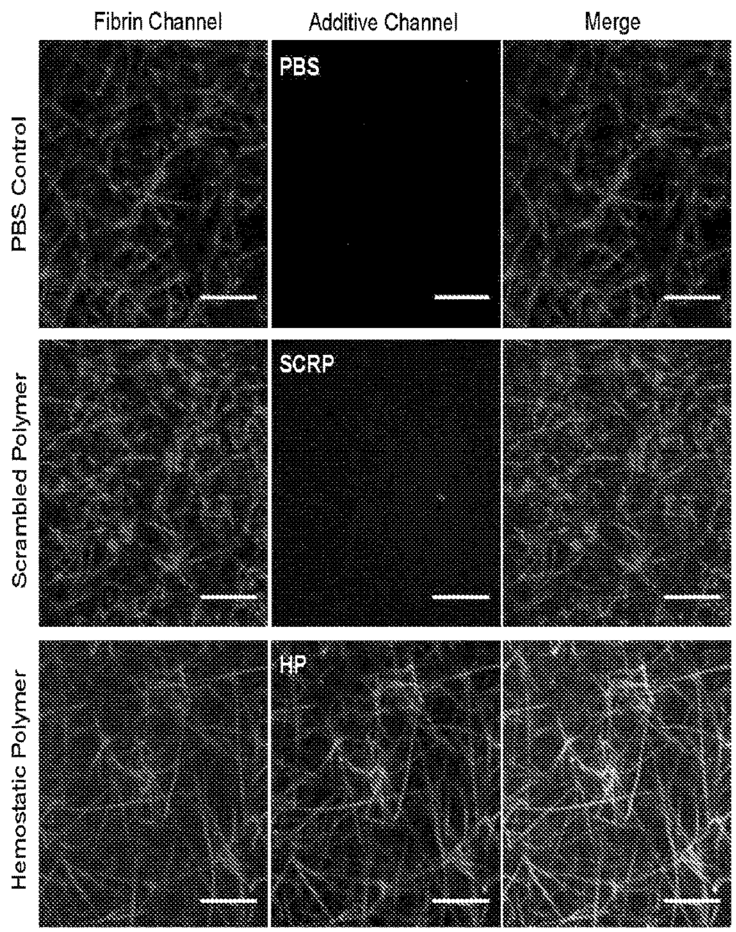
FIG. 2A-2D. Hemostatic polymers are integrated throughout the fibrin network and alter fibrin nanostructure.
Figure 2D:
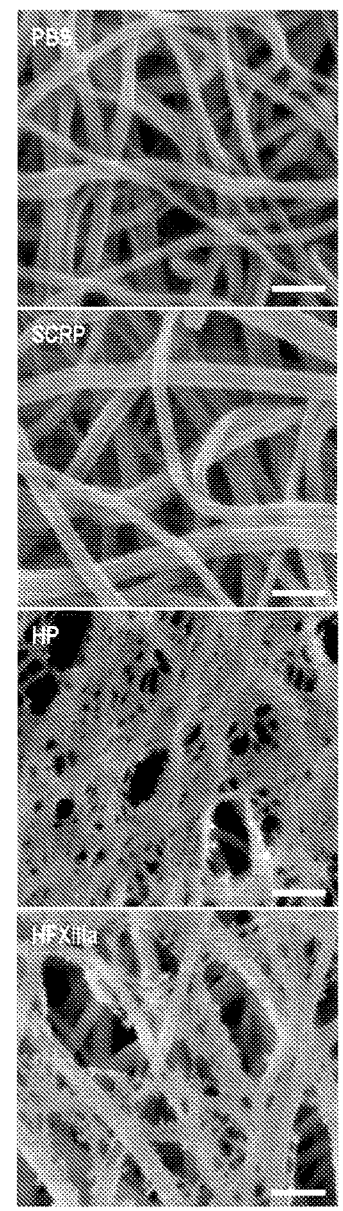
Figure 2B:
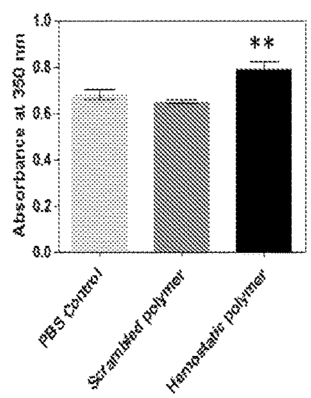

Confirmation of HP integration into fibrin was completed using confocal imaging. Fluorescent HP (fHP) and SCRP (fSCRP) were synthesized using a polymer backbone with a target composition of 78% HEMA, 2% fluorescein O-methacrylate, and 20% NHSMA. Pure fibrin clots were formed using a re-calcified solution of 3 mg/mL Alexa-Fluor 546-labeled fibrinogen, 0.167 IU/mL thrombin, and 5 μM fHP, fSCRP, or an equal volume of PBS. Visualization with confocal microscopy showed that fHP fluorescence exhibited fiber morphology which coincided precisely with fluorescence from fibrin fibers (FIG. 2A). fSCRP fluorescence, however, showed no distinct morphology, demonstrating that incorporation of fibrin-specific peptide sequences in HP is necessary for polymer integration into fibrin networks. fHP fluorescence appeared evenly-distributed throughout fibrin fibers suggesting that HPs are actively participating in the fibrin polymerization process. This is further supported by turbidity measurements collected during fibrin clot formation (FIG. 2B). Turbidity measurement is a well-established method for tracking clot formation as well as potential changes in clot structure. As fibrin fibers form, clotting solutions become more turbid. Final turbidities of fully-formed fibrin clots are used to indicate whether changes in fibrin structure have occurred since alterations in fiber diameter affect the transmission of wavelengths through the clot. Interestingly, turbidity increased at a faster rate in clotting solutions with HP. This indicates that fibrin fiber formation is accelerated in its presence which is highly possible since HP was designed to crosslink fibers during fibrin polymerization. A plateau in turbidity signifies the end of fibrin formation. HP-integrated clots had significantly greater turbidities compared to control clots. Therefore, clot structure was further investigated using permeation studies and SEM imaging.

Figure 2C:
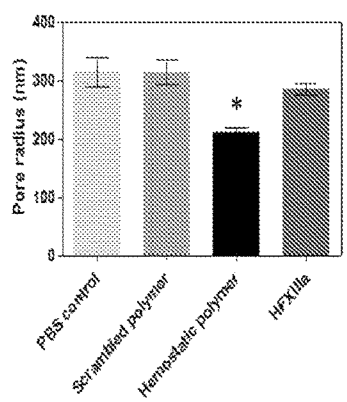

Reduced pore size of fibrin clots is an indicator of successful fibrin crosslinking. In permeation studies, re-calcified clotting solutions containing 3 mg/mL FXIII-depleted fibrinogen, 0.167 IU/mL thrombin, and 5 μM HP, SCRP, 10 μg/mL human FXIIIa (HFXIIIa) or an equal volume of PBS were placed in 3-mL syringe barrels and allowed to clot for 1 hr. HFXIIIa treatment was included as a positive control for crosslinking. Hydrostatic pressure was used to generate water flow through fully-formed fibrin clots. Flow rates were used to extrapolate pore size as previously described in literature [Wufsus 2013]. Fluid flow through HP-integrated fibrin clots was recognizably hindered and pore radii were reduced to 212±11 nm from control pore radii of 315±43 and 314±37 calculated from PBS and scrambled polymer controls, respectively (FIG. 2C). Interestingly, 5 μM HP was more effective at reducing pore size than 10 μg/mL HFXIIIa, which produced pore radii of 286±18 nm. SEM imaging showed trends in pore size consistent with results from the permeation study (FIG. 2D). Furthermore, additional changes in clot structure were observed including the presence of thinner fibers and a markedly increased fiber density. Alterations in clot structure are similar those observed in FXIIIa-treated clots, thus supporting the crosslinking mechanism of HP.

Hemostatic Polymer-Induced Modification of Fibrin Formation and Degradation

Figure 3A:
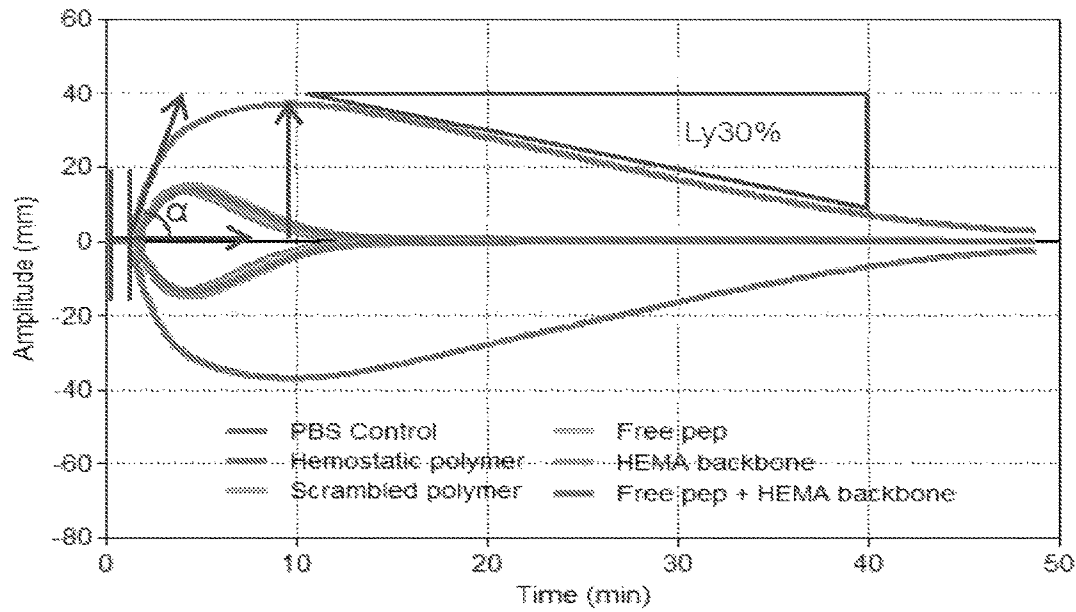
FIGS. 3A-3F. Fibrin-crosslinking hemostatic polymers accelerate clot formation and increase clot strength and resistance to fibrinolysis in an in vitro fibrinolytic system.
Figure 3B:
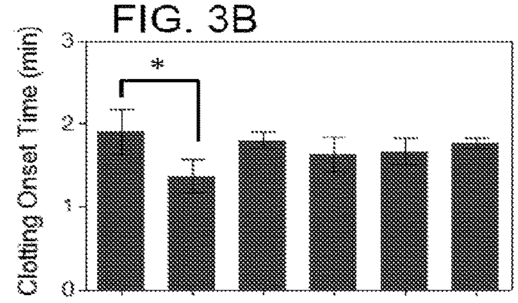
Figure 3C:
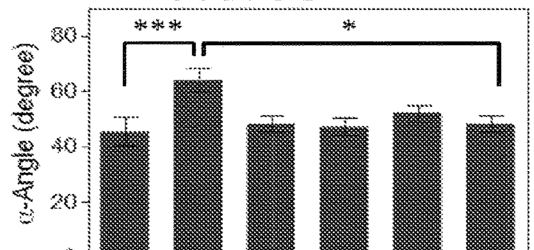
Figure 3D:
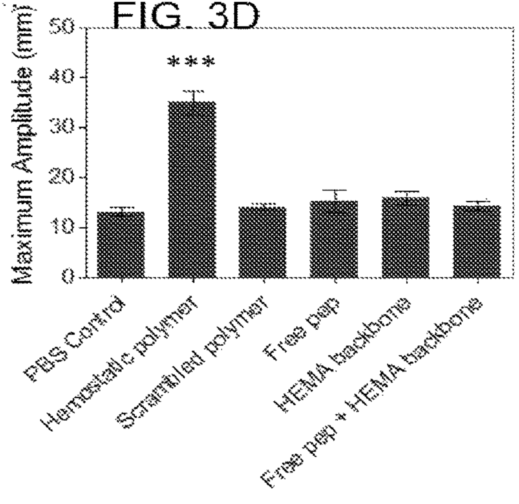
Figure 3E:
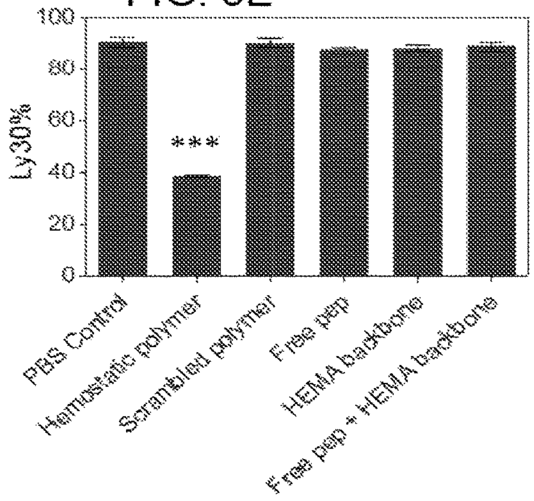
Figure 5:
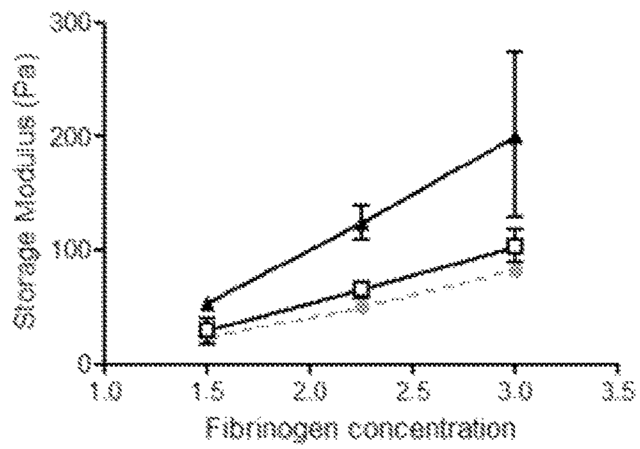
FIG. 5. HP-induced crosslinking increases fibrin clot strength. Effects of HP on clot strength was evaluated at low (1.5 and 2.2 mg/mL) and average (3.0 mg/mL) fibrinogen concentrations. Storage moduli, a measure of clot elasticity, was measured using a rheometer with 0.1% strain oscillations at 1 Hz. At all three fibrinogen concentrations, storage moduli of fully-formed HP-modified fibrin (solid triangles) was significantly greater than fibrin with PBS (circles) and SCRP (open squares). HP-induced crosslinking increased storage moduli of 1.5 and 2.2 mg/mL fibrin clost to those of untreated 2.2 and 3.0 mg/mL fibrin clots, respectively. Statistical significance was determined using one-way ANOVA with Tukey post hoc test (p<0.001).
Figure 6A:
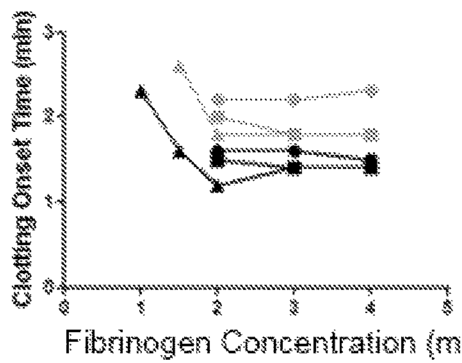
FIGS. 6A-6D. FCP accelerates clot formation and increases clot strength and resistance to fibrinolysis in pure fibrin systems. TEG was used to measure the (FIG. 6A) clotting onset time, (FIG. 6B) clotting rate, (FIG. 6C) clot strength, and (FIG. 6D) percent clot lysis 30 minutes after time to MA of purified fibrin clots formed with 5 μM FCP (black) or PBS (grey). The effects of FCP on clot properties were evaluated in 1-5 mg/mL fibrinogen, 0.5 IU/mL thrombin, and 3 μg/mL plasmin (▲), 4 μg/mL plasmin (■), or 5 μg/mL plasmin (●). Fibrin clots consistently formed with shorter clotting onset times and at faster rates and were stronger and more resistant to lysis regardless of fibrinogen and plasmin concentration.
Figure 6B:
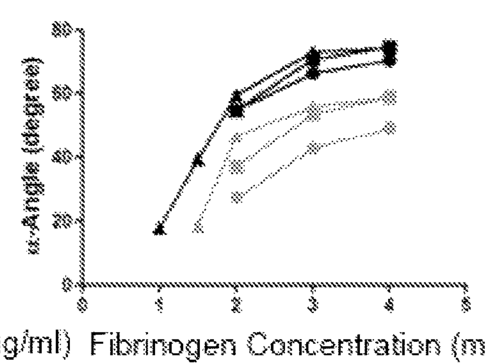
Figure 6C:
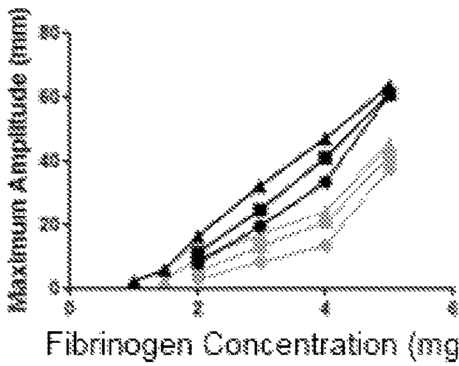
Figure 6D:
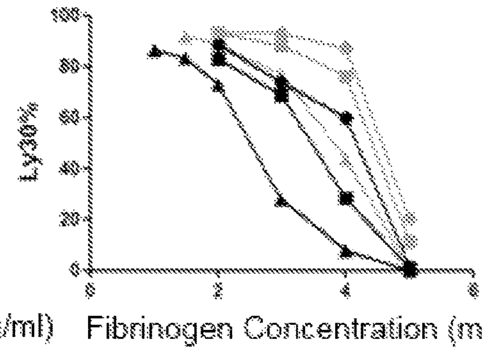
Figure 7A:
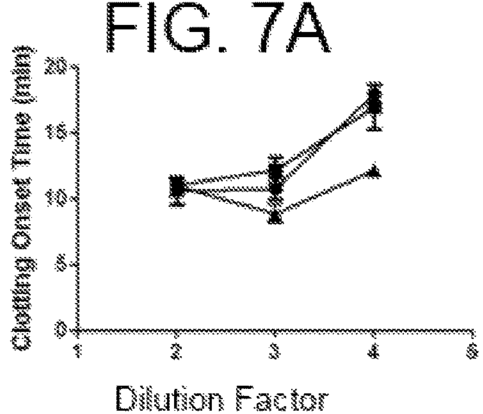
FIGS. 7A-7D. FCP increases clot strength and resistance to fibrinolysis in diluted whole blood. Hemodilutions were treated with PBS (●), 5 μM FCP (■), and 5 μM scrFCP (▲). TEG was used to measure the (FIG. 7A) clotting onset time, (FIG. 7B) clotting rate, (FIG. 7C) clot strength, and (FIG. 7D) percent clot lysis 30 minutes after time to MA. Fibrinolysis was inhibited in FCP-treated clots. These results are expressed as averages with bars for standard deviation (n=2). Statistical significance was determined using one-way ANOVA with Tukey post hoc test (*p≤0.05 at a single dilution, **p≤0.05 at all dilutions).
Figure 7B:
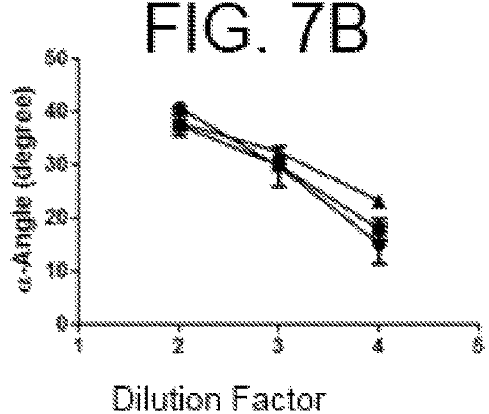
Figure 7C:
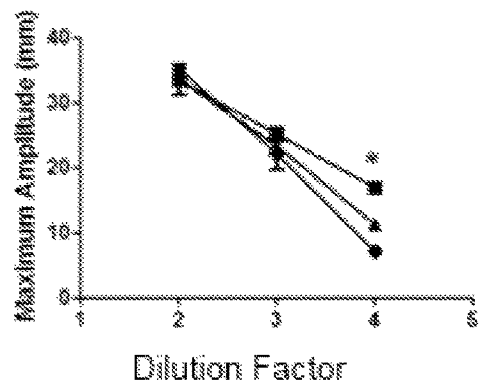
Figure 7D:
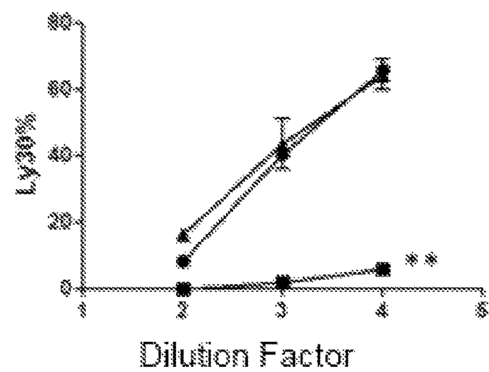

Thromboelastography (TEG) is a viscoelastic tool that tracks clot strength (or shear modulus) over time. TEG traces plot clot strength over time. Thus, clot formation and degradation is signified by an increase and decrease of clot strength, respectively. Quantitative values for clotting onset time (R), clotting rate (α-angle), maximum clot strength (MA), and percent of clot lysed 30 minutes after time to MA (Ly30%) can be extracted from TEG traces (FIG. 3A). An in vitro hyperfibrinolytic system with low fibrinogen content and high plasmin concentration was evaluated using TEG to determine the effects of HP under coagulopathic conditions. Fibrinogen circulates in blood at 1.5-3.0 mg/mL. [Lord 2007] 1.5 mg/mL fibrinogen was used to determine the ability of HP to crosslink at lower fibrinogen levels that would be observed in patients after the early stages of severe hemorrhage. [Fries] A 1:1 molar ratio of HP to fibrinogen, translating to 5 μM HP, was used to provide 2 possible binding sites per polymer, the minimum requirement for crosslinking. Consistent with turbidity results in FIG. 2B, HP presence in clotting solutions accelerated fibrin fiber formation as evident by earlier clotting onset times and 23-41% faster clotting rates relative to controls (FIG. 3B-C). Again, this is likely due to crosslinking of forming fibers. Binding of HP to multiple fibrin monomers may also increase local monomer concentrations thus facilitating fibrin polymerization. Clot strength was 2.5 times greater in HP-modified clots compared to controls (FIG. 3D). In the absence of plasmin, no difference in clot strength was observed between HP-modified and control clots (FIG. 5). Not surprisingly, this demonstrates that the presence of plasmin during clot formation prevents clots from achieving the maximum clot strength that they otherwise would have reached and illustrates the ability of HP-induced crosslinking to counteract plasmin degradation and conditionally increase clot strength. The effect of HP on clot degradation is further observed in quantification of Ly30%. In fibrin clots with PBS, SCRP, and free peptide and HEMA polymer controls, 88-90% lysis occurred by 30 minutes after time to MA (FIG. 3E). In stark contrast, HP-modified fibrin clots experienced 39±0.45% lysis within the same time frame. Indeed, TEG curves in FIG. 3A clearly illustrate the extended lifetime of HP-modified clots (50 minutes versus 15 minutes). These studies were repeated in a range of biologically-relevant fibrinogen and plasmin concentrations, which showed all-around improved clotting parameters (FIGS. 6A-6D). At a fixed concentration of 5 μM HP, Ly30% curves approached 0% lysis with increasing fibrinogen concentration, thus, suggesting a dependence of HP performance on fibrin concentration which is consistent with the proposed mechanism of fibrin crosslinking.

Figure 8:
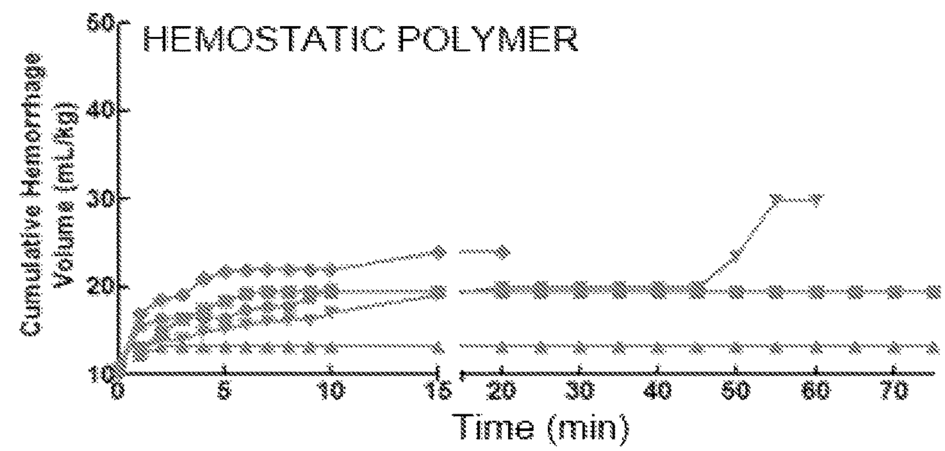
FIG. 8. Cumulative hemorrhage volumes in rat femoral artery injury models. Graphs show cumulative hemorrhage volume of each rat in one of three treatment groups (HP, SCRP, or rat albumin) after release of clamps at t=0. Five rats were completed per treatment group. An albumin control group was included to account for effect of molecular weight (65 kDa) on intravascular osmotic pressure.
Figure 8:
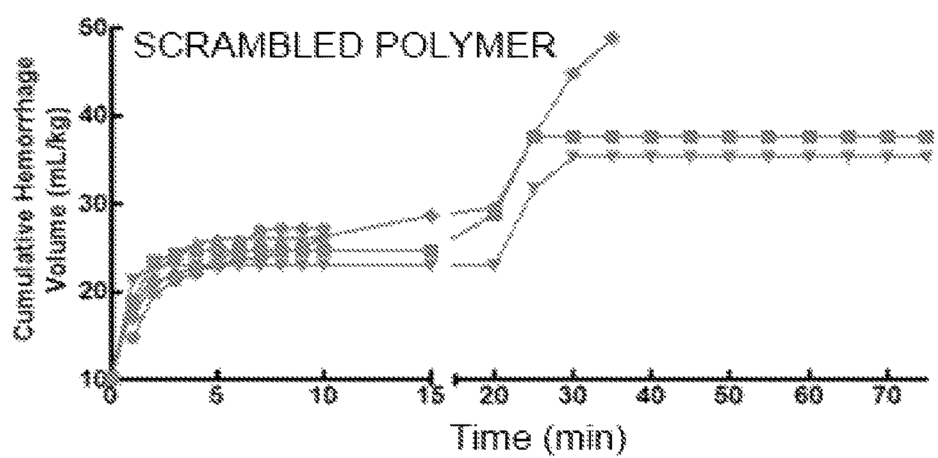
Figure 8:
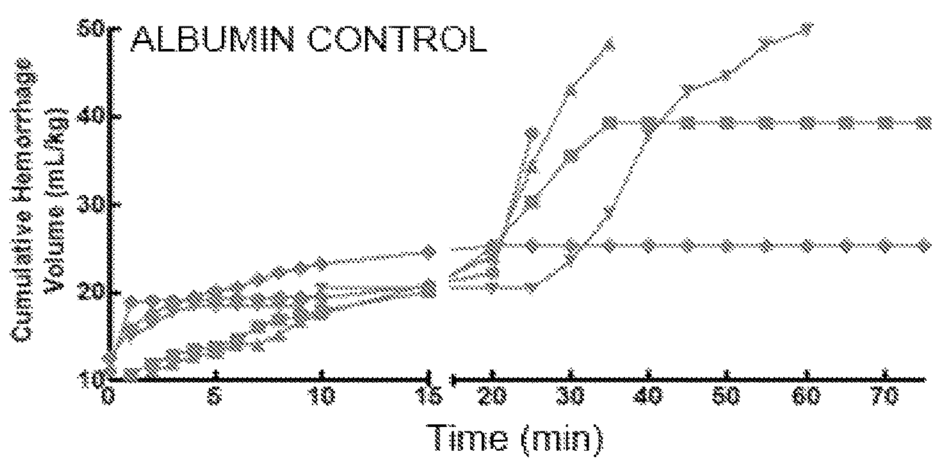

A TEG study using diluted whole blood was conducted to determine if the same HP-induced clotting behavior would be observed in the presence of all blood components. 1:1, 1:2, and 1:3 Hemodilutions in 0.9% saline were used to mimic dilution effects of fluid resuscitation used to treat hypovolemia after massive blood loss. As observed in pure fibrin, HP-modified blood clots experienced significantly less lysis than controls—0.0±0.0%, 2.0±2.8%, and 5.9±3.2% lysis for 1:1, 1:2, and 1:3 hemodilutions, respectively, compared to 16±1.9%, 44±7.6%, and 64±4.7% in scrambled controls (FIG. 7A-7D). Therefore, HP-modified blood clots are highly resistant to fibrinolysis even when formed from very dilute blood. Consistent with results in pure fibrin, no differences were observed in the absence of clot lysis which is beneficial for preventing thrombus formation (FIG. 8).

Figure 3F:
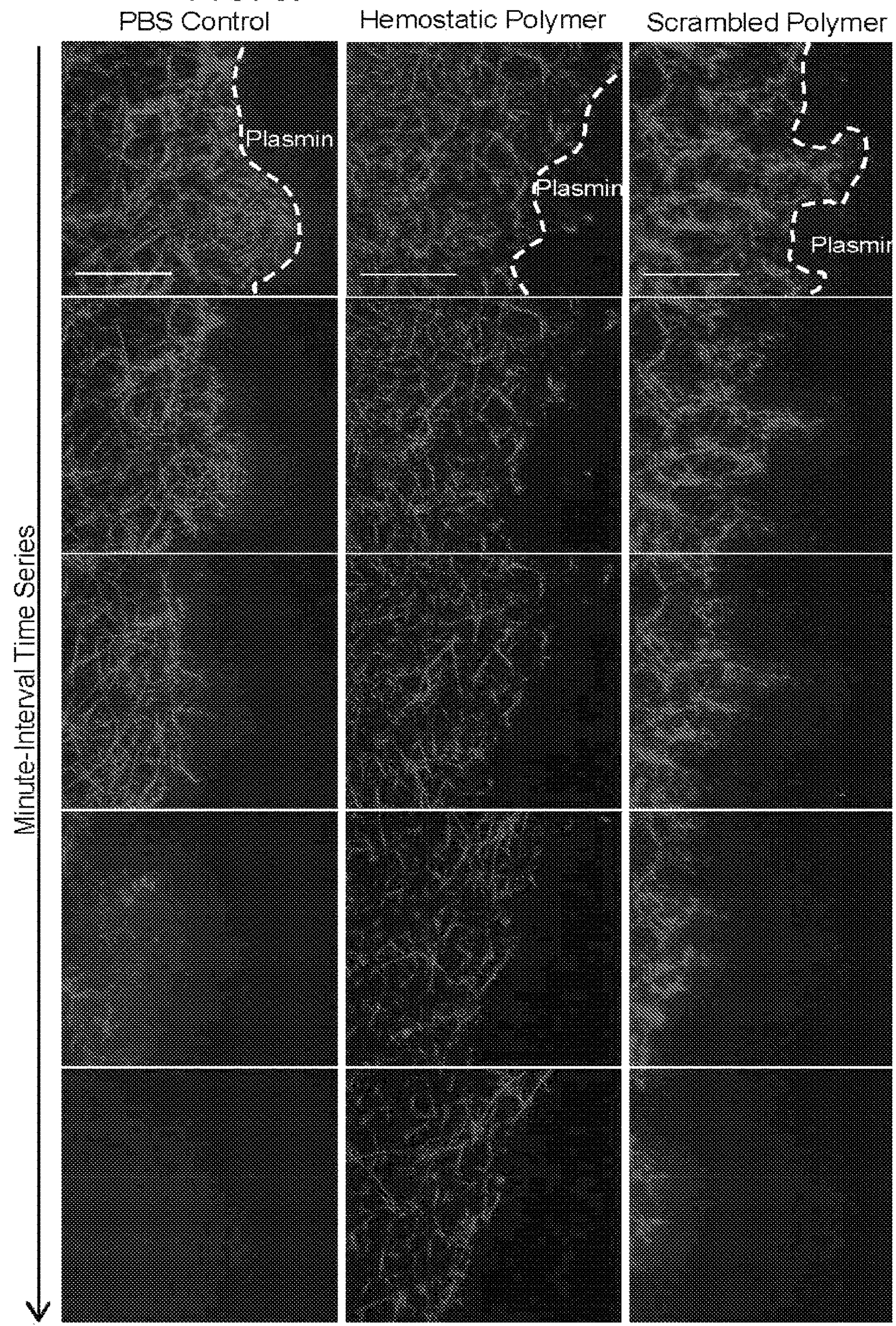

Time-lapsed confocal imaging was completed on HP-crosslinked fluorescent fibrin clots to visualize fibrinolysis in a single z-plane. Clots were formed using the same clotting solution used in previous confocal imaging studies. A high concentration of plasmin was added to the edge of fully-formed clots and images were taken at the leading edge to track clot breakdown. Images at 1-minutes intervals are shown (FIG. 3F). Despite the high plasmin concentration, it took twice as long for HP-integrated fibrin to degrade compared to fibrin with PBS and SCRP. Interestingly, HP-modified fibers could be seen resisting breakdown as evident by increasing tension in fibrin fibers and an unzipping action while control clots were readily degraded with no observable resistance.

Hemostatic Efficacy of HP in a Rat Femoral Artery Injury Model

Figure 4A:
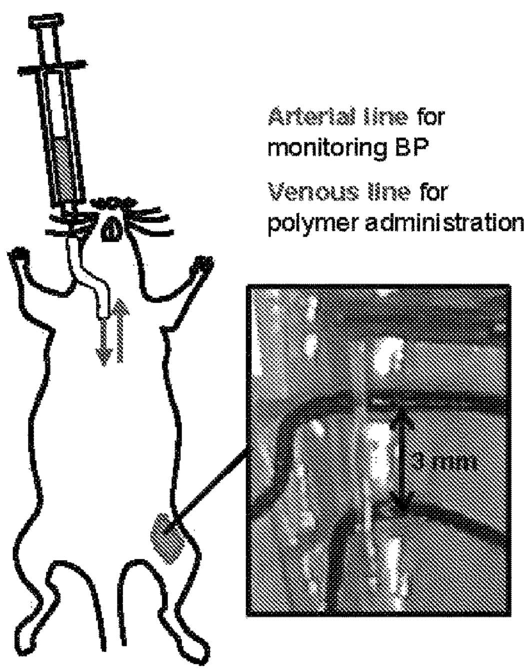
FIGS. 4A-4E. Hemostatic polymers reduce blood loss, improve vitals, and reduce fluid resuscitation requirements in a rat femoral artery injury model.
Figure 9:
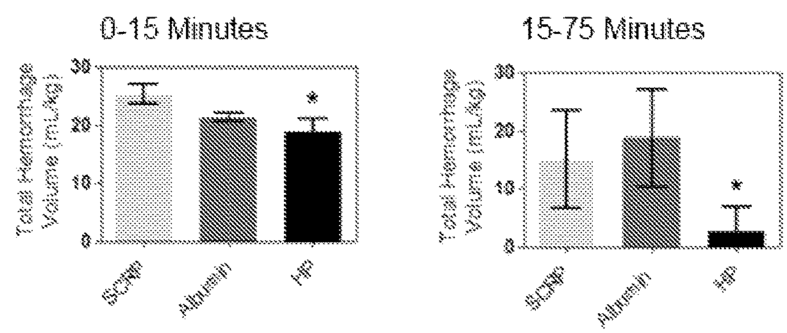
FIG. 9. Total hemorrhage volumes during the free bleeding phase and fluid resuscitation phase in the rat femoral artery injury model. During the free bleeding phase (left), HP-treated rats bled significantly less than SCRP-treated rats. During the fluid resuscitation phase (right), HP-rats bled significantly less than rats injected with albumin. Results are expressed as averages with bars for standard deviation. Statistical significance was determined using a 1-way ANOVA with Tukey post hoc test (*p≤0.05).
Figure 9:
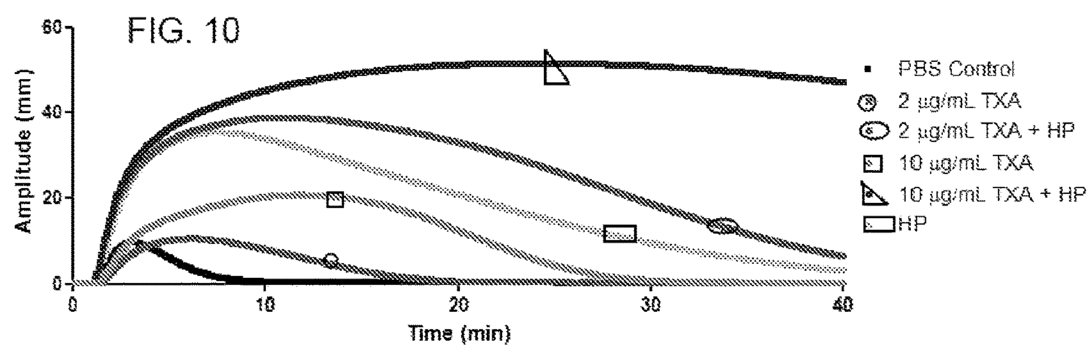

In trauma, major blood loss results in dramatic drops in blood pressure (BP) which severely limits perfusion of vital organs and other tissues. The body may restore blood pressure naturally through the transport of water from the intracellular and interstitial compartments into the intravascular space but more often medical intervention by infusion of crystalloid or colloidal solutions is needed. In either instance, clots are often not strong enough to withstand increased blood pressures and rebleeding occurs. To evaluate the competency of HP-modified clots under such conditions, a rat femoral artery injury model with a fluid resuscitation phase was treated with a volume control (PBS), a colloidal control (rat albumin), 15 mg/mL SCRP, or 15 mg/mL HP, a dose replicating concentrations used in vitro and exhibiting no acute liver or kidney toxicity 24 hours after intravenous administration (FIG. 9). The work flow for these studies is shown in FIG. 4A (and see Table 3). In this model, the femoral artery in an anesthetized rat was isolated and clamped proximally and distally. A 3-mm longitudinal incision was made between the clamps. HP and controls were administered via a venous line in the jugular vein. After 5 minutes of circulation time, rats were normalized to a starting blood pressure of 60 mm Hg by a controlled catheter hemorrhage. Clamps were then removed to allow bleeding from the injury. Rats bled freely in the first 15 minutes after clamp removal. After 15 minutes, isotonic saline infusion was used to maintain blood pressures above 60 mm Hg.

TABLE 3

Femoral Artery Injury Model Timeline

| Pre-injury phase | Post-injury phase | |
|---|---|---|
| t = −8 min<br>Polymer injection<br>t = −3 min<br>Catheter hemorrhage to lower BP to 60 mm Hg | 0 ≤ t < 15 min<br>Free bleeding<br>Clamps preventing bleeding from the incision are removed at t = 0 | t ≤ 15 min<br>Fluid resuscitation<br>If BP <60 mm Hg, an isotonic saline solution is infused at 3 mL/min/kg till BP rises to 60-65 mm Hg. Maximum infusion volume is 60 mL/kg. |

Figure 4B:
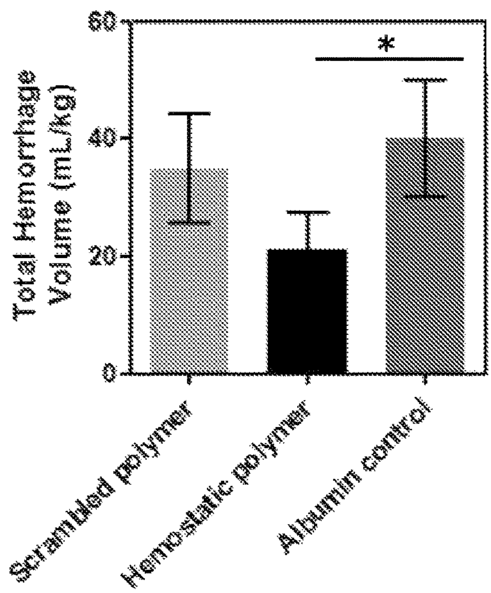
Figure 4C:
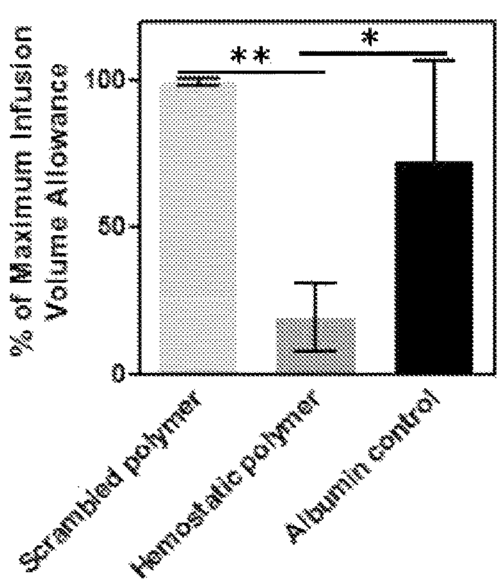
Figure 4D:
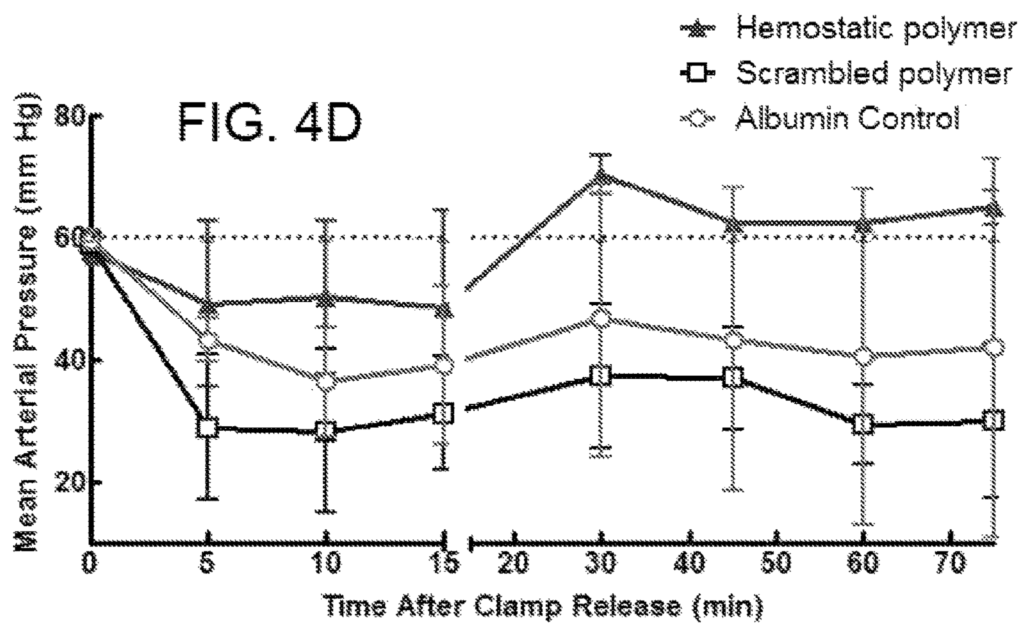
Figure 4E:
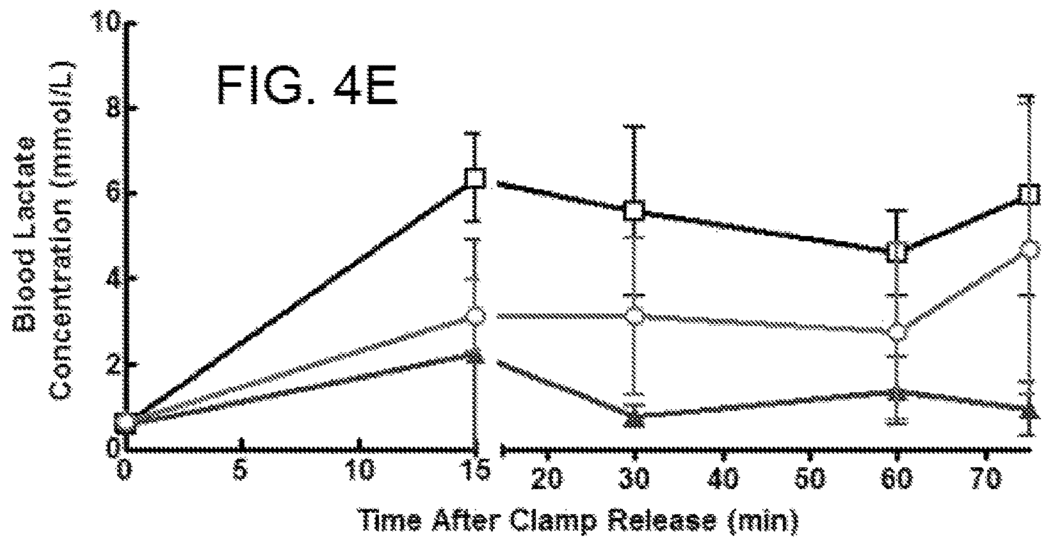

HP-treated rats had significantly less cumulative hemorrhage volume during the 75-minute protocol suggesting an increased hemostatic ability (FIG. 4B). Due to reduced blood loss HP-treated rats required 5-times less saline infusion to maintain blood pressure above 60 mm Hg (FIG. 4C, 4E). In addition, lactate acid concentrations measured right before fluid resuscitation (t=15 min) and 15, 45, and 60 min after the start of fluid resuscitation (t=30, 60, 75 min) in blood were significantly less, indicating improved tissue perfusion and oxygen delivery (FIG. 4D).

Collectively, these results demonstrate that fibrin clotting kinetics, clot strength, and resistance to fibrinolysis can be modulated by addition of fibrin-crosslinking polymers during fibrin polymerization. Here, using a linear HEMA polymer with multivalent display of fibrin-binding peptides, we were able to accelerate fibrin polymerization while increasing fibrin mechanical and chemical stability. Introduction of synthetic polymers into the fibrin network can be additionally investigated to weaken clot structure in thrombotic diseases. Thus, there is broad applicability of affinity-based polymer technology for addressing hemostasis and thrombosis.

TABLE 4

Comprehensive and hepatic panel results for rats 24 hours after hemostatic polymer injection.

| | No Treatment | | 15 mg/kg Hemostatic Polymer | | 30 mg/kg Hemostatic Polymer | |
|---|---|---|---|---|---|---|
| | Rat 1 | Rat 2 | Rat 1 | Rat 2 | Rat 1 | Rat 2 |
| Sodium | 139 | 139 | 141 | 141 | 139 | 137 |
| Potassium | 4.0 | 5.1 | 4.6 | 4.3 | 4.1 | 5.5 |
| Chloride | 101 | 102 | 101 | 100 | 100 | 98 |
| Carbon Dioxide, Total | 28 | 27 | 28 | 30 | 27 | 29 |
| Anion Gap | 10 | 10 | 12 | 11 | 12 | 10 |
| Glucose | 320 | 338 | 300 | 241 | 294 | 342 |
| Urea Nitrogen | 14 | 13 | 15 | 15 | 14 | 14 |
| Creatinine | 0.26 | 0.24 | 0.23 | 0.22 | 0.19 | 0.24 |
| Protein (Total) | 4.8 | 4.5 | 5.6 | 5.7 | 5.6 | 5.3 |
| Albumin | 1.3 | 1.4 | 1.2 | 1.5 | 1.4 | 1.3 |
| Bilirubin (Total) | 0.1 | 0.3 | 0.3 | 0.1 | 0.3 | 0.2 |
| Bilirubin (Direct) | <0.1 | 0.1 | 0.1 | <0.1 | <0.1 | 0.1 |
| Calcium | 10.0 | 10.1 | 10.2 | 10.8 | 10.5 | 10.3 |
| AST (GOT) | 79 | 105* | 195 | 89 | 143 | 81 |
| Alkaline Phosphatase (Total) | 382 | 285 | 305 | 371 | 401 | 443 |
| ALT (GPT) | 41 | 42 | 58 | 54 | 82 | 51 |

*Hemolysis present. Hemolysis interferes with this test method giving elevated results.

Methods

Synthesis and Characterization of Hemostatic Polymers (HP) and Scrambled Polymer Controls (SCRP).

All materials for polymer backbone synthesis were purchased from Sigma-Aldrich. The HP backbone with a target composition of 80% (hydroxyethyl) methacrylate (HEMA) and 20% N-hydroxysuccinimide methacrylate (NHSMA) was synthesized using RAFT polymerization. For a typical synthesis, 310 uL HEMA (2.56 mmol), 117.2 mg NHSMA (0.640 mmol), 1 mL AIBN (0.876 mg/ml in DMAc, 0.0053 mmol), and 4.47 mg CPADB (0.016 mmol) were dissolved in a 5-mL reaction vessel with 3.02 mL DMAc for a final monomer concentration of 0.6 M. The reaction mixture was purged with argon for 10 minutes and reacted under stirring conditions at 70° C. for 24 hr. Fluorescent hemostatic polymer (fHP) and scrambled polymer control (fSCRP) were synthesized by altering the composition of pHB to 78% HEMA and 2% fluorescein O-methacrylate and maintaining 20% NHSMA. Polymers were precipitated in ether, dissolved in DMAc, and reprecipitated in ether to remove unreacted monomers. Polymers were then dried and stored in a vacuum-sealed oven. Dithiobenzoate groups were removed in a subsequent reaction with a 20:1 molar ratio of AIBN to polymer. Transition of the solution from pink to clear was a positive indicator that the endcapping reaction was near or at completion. Degree of polymerization and monomer composition were determined using $H^1$ NMR, and polydispersity and molecular weight were measured using GPC. The absence of CTA peaks on $H^1$ NMR was used to confirm removal of dithiobenzoate groups. Fibrin-binding peptides with the sequence Ac-Y(DGI)C(HPr)YGLCY-IQGK (SEQ ID NO: 1; Ac=acetylation of N-terminus, DGI=D-glutamic acid, HPr=hydroxyproline, cyclized via C3-C8 monodisulfide bond) were conjugated to NHS reactive groups on pHB via the ε-amine on the C-terminus lysine under organic basic reaction conditions as reported by Yanjarappa et al [Yanjarappa 2006]. Peptides with a scrambled FBP sequence Ac-YICGQ(DGI)AC(HPr)LYGK (SEQ ID NO: 2) were conjugated to NHS groups on pHB for the scrambled polymer control. After 24 hr, reaction solutions were transferred to snakeskin dialysis tubing with 10 kDa MWCO and dialyzed against PBS for 2 days to remove free peptide. Polymers were then dialyzed against DI water for 2 days to remove salts from the PBS and lyophilized. The number of peptides per polymer was determined by measuring absorption at 280 nm using a Nanodrop 2000 UV-vis spectrophotomer.

Confocal Imaging of Pure Fibrin Clots to Show Co-Localization of Hemostatic Polymers and Fibrin.

Fibrin clots were prepared in chambered coverslips using 0.5 mL clotting solution with the following final concentrations: 3 mg/mL fibrinogen spiked with 1% Alexa Fluor 546®-labeled fibrinogen (Life Technologies F13192), 0.167 IU/mL thrombin, 10 μM $CaCl_2$, and 5 μM fluorescent HP, 5 μM fluorescent SCRP, or an equal volume of PBS. After 1 hr, clots were imaged with a Zeiss LSM 510 inverted confocal microscope using a 63× objective lens. Lasers with 488 nm and 543 nm wavelength were used to excite polymers and fibrinogen, respectively. BP 505-530 and LP 560 were used to isolate signal from polymers and fibrinogen, respectively. To prevent bleed-through, only one laser was turned on at a time during image acquisition. Image overlays were completed in ImageJ.

Clot Permeation Studies for Determination of Pore Size.

Permeation studies were completed as previously described in literature [Wufsus 2013]. Fibrin clots were formed in 3-mL syringe barrels using 1 mL solution containing 3 mg/mL FXIII-depleted fibrinogen (Enzyme Research Laboratories P1 FIB), 0.167 IU/mL thrombin, and 10 mM $CaCl_2$ in HEPES-NaCl buffer with PBS, 5 μM SCRP, 5 μM HP, or 10 mg/mL HFXIIIa (Enzyme Research Laboratories HFXIIIa 1314). Clots were allowed to form for 1 hour after which they were connected via ¾" inner diameter tubing to a 50-mL syringe barrel filled with water and elevated 27 cm from the benchtop. Volumetric flow rate was measured and pore size calculated using Darcy's Law and a model for pore radius by Carr and Harding.

$$\text{Darcy's Law, } Da = \frac{Vnh}{Atp}$$

$$\text{Carr and Harding, } R_P = \frac{0.5093}{Da^{-1/2}}$$

SEM Imaging of Pure Fibrin Clots.

Fibrin clots were prepared in 24-well plates using 0.5 mL clotting solution with the following final concentrations: 3 mg/mL fibrinogen, 0.167 IU/mL thrombin, 10 μM $CaCl_2$, and 5 μM HP, 5 μM SCRP, 10 μg/mL Factor XIIIa, or an equal volume of PBS. After 1 hr, clots were fixed in 2.5% glutaraldehyde in DI water for 1 hr. Clots were then washed 5 times (5 min per wash) in DI water and dehydrated in increasing percentages of alcohol (25, 50, 75, 100, 100% ethanol, 10 min per ethanol percentage). Samples were chemically dried by immersion in 1:3 volume ratio of hexamethyldisilazane to ethanol for 15 min and subsequently in pure hexamethyldisilazane for 15 min. Finally, samples were placed on filter paper and dried overnight in a chemical hood.

Movie Acquisition for Lysing Fibrin Clots.

Clots were formed as described for confocal co-localization studies. Time series of lysing clots were taken using only the fibrin channel. A 10 μg/mL plasmin solution was placed at the edge of fibrin clots, and time-lapsed images were taken every 10 seconds to track clot degradation. ImageJ was used to set movies to 10 fps (100× faster than actual speed).

Plasminogen Activation by HP-Modified Fibrin Clots.

Purified fibrin clots were prepared with the same clotting solution as those used for SEM imaging in a 48-well plate. 0.5 mM chromogenic plasmin substrate (Innovative Research Inc.), 1.8 nM tPA, 1 μM plasminogen, and 10 μM $CaCl_2$ in HEPES-NaCl buffer was applied over the top of the clot. Samples were collected every 30 min for 3 hours, and absorbance at 405 nm was measured using a Nanodrop spectrophotometer.

In Vitro Evaluation of HPs Using Thromboelastography.

In a typical TEG experiment, a 360-μL clotting solution is added to a cup in a TEG® 5000 Thromboelastograph® Hemostasis Analyzer system. A pin attached to a torsion wire is submerged into the center of the cup. When the device is started, the cup oscillates around the stationary pin and as the clot forms, the movement of the pin becomes coupled with the cup. The amplitude of oscillatory motion of the pin, which is directly proportional to clot strength, is measured over time. Other measures that can be extracted from TEG traces include clot onset time (R), clotting rate (α-angle in degrees), maximum clot strength (maximal amplitude in mm, MA), and the extent of lysis 30 minutes after the time to MA (ly30%). HP, SCRP, pHB stock solutions were made at 250 μM and FBP stock solution at 4 mM. 7.2 μL volumes were added to clotting solutions for final concentrations of 5 μM and equivalent peptide concentration. For purified fibrin systems, the clotting solution had final concentrations of 1.5 mg/mL plasminogen-depleted fibrinogen (Enzyme Research Laboratories FIB 1), 0.5 IU/mL thrombin (Stago Fibri Prest® Automate 5), 2 μg/mL plasmin (Enzyme Research Laboratories), and 10 mM $CaCl_2$ in pH 7.4 NaCl-HEPES buffer (44 mM HEPES, 2 mM $CaCl_2$, 140 mM NaCl). Fibrinogen was added to the enzymes and $CaCl_2$ immediately before each TEG run. For evaluation in hemodilutions, citrated fresh human blood was diluted at 1:1, 1:2, and 1:3 parts blood to 0.9% saline. 333 μL of Hemodilutions was mixed with 20 μL 0.2M $CaCl_2$ solution and 7.2 μL volumes of HP or controls.

Hemostasis in a Rat Femoral Artery Injury Model.

Rats were anesthetized using isoflurane and 0.1 mL ketamine-xylazine cocktail injection in the hindlimb. The carotid artery and jugular vein were catheterized for monitoring of blood pressure and for intravenous injection of polymers, respectively. The femoral artery in the left leg was isolated and microsurgical clamps were placed proximally and distally to prevent bleeding from a 3-mm longitudinal incision made after clamping. PBS, HP, SCRP, or rat albumin (10 mg/mL) was administered over 1.5 minutes at a 15 mg/kg dose (n=5). 5 minutes after injection, catheter bleeds were completed via the arterial line to normalize all starting blood pressures to ~60 mm Hg. At t=0 min, clamps were removed from the femoral artery and the injury was allowed to bleed freely for 15 min. For t>15 min, saline infusion at 1 mL/min was used to maintain BP above 60 mm Hg. Blood gas measurements were taken before the incision (baseline), before fluid resuscitation (t=15 min), and during the fluid resuscitation phase (t=30, 60, 75 min) to monitor blood pH, gas levels, ion concentrations, and lactate concentration. Blood was collected using pre-weighed gauze to track blood loss over time.

REFERENCES

1. Sauaia, A. et al. Epidemiology of trauma deaths: a reassessment. *The Journal of trauma* 38, 185-193 (1995).
2. Davenport, R. et al. Functional definition and characterization of acute traumatic coagulopathy. *Critical care medicine* 39, 2652-2658 (2011).
3. Raza, I. et al. The incidence and magnitude of fibrinolytic activation in trauma patients. *Journal of thrombosis and haemostasis: JTH* 11, 307-314 (2013).
4. Brohi, K., Singh, J., Heron, M. & Coats, T. Acute traumatic coagulopathy. *The Journal of trauma* 54, 1127-1130 (2003).
5. Nystrup, K. B., Windelov, N. A., Thomsen, A. B. & Johansson, P. I. Reduced clot strength upon admission, evaluated by thrombelastography (TEG), in trauma patients is independently associated with increased 30-day mortality. *Scandinavian journal of trauma, resuscitation and emergency medicine* 19, 52 (2011).
6. Moore, F. A., Moore, E. E. & Sauaia, A. Blood transfusion. An independent risk factor for postinjury multiple organ failure. *Archives of surgery* (Chicago, Ill.: 1960) 132, 620-624; discussion 624-625 (1997).
7. Lord, S. T. Fibrinogen and fibrin: scaffold proteins in hemostasis. *Current opinion in hematology* 14, 236-241 (2007).
8. Hennink, W. E. & van Nostrum, C. F. Novel crosslinking methods to design hydrogels. *Adv Drug Deliv Rev* 54, 13-36 (2002).
9. Theusinger, O. M., Baulig, W., Asmis, L. M., Seifert, B. & Spahn, D. R. In vitro factor XIII supplementation increases clot firmness in Rotation Thromboelastometry (ROTEM). *Thrombosis and haemostasis* 104, 385-391.
10. Hethershaw, E. L. et al. The effect of blood coagulation factor XIII on fibrin clot structure and fibrinolysis. *Journal of thrombosis and haemostasis: JTH* 12, 197-205 (2014).
11. Kolodziej, A. F. et al. Fibrin specific peptides derived by phage display: characterization of peptides and conjugates for imaging. *Bioconjugate chemistry* 23, 548-556 (2012).
12. Overoye-Chan, K. et al. EP-2104R: a fibrin-specific gadolinium-Based MRI contrast agent for detection of thrombus. *Journal of the American Chemical Society* 130, 6025-6039 (2008).
13. Vymazal, J. et al. Thrombus imaging with fibrin-specific gadolinium-based MR contrast agent EP-2104R: results of a phase II clinical study of feasibility. *Investigative radiology* 44, 697-704 (2009).
14. Yanjarappa, M. J., Gujraty, K. V., Joshi, A., Saraph, A. & Kane, R. S. Synthesis of copolymers containing an active ester of methacrylic acid by RAFT: controlled molecular weight scaffolds for biofunctionalization. *Biomacromolecules* 7, 1665-1670 (2006).
15. Wufsus, A. R., Macera, N. E. & Neeves, K. B. The hydraulic permeability of blood clots as a function of fibrin and platelet density. *Biophysical journal* 104, 1812-1823 (2013).

Example 2: Synergistic Effect of Hemostatic Polymer and TXA

This example demonstrates the synergistic effect of hemostatic polymer HP and tranexamic acid (TXA), a clinically-approved antifibrinolytic drug. Fibrin clots were formed with 1.5 mg/mL fibrinogen and 0.5 IU/mL thrombin with the addition of 2 μg/mL plasmin to generate an in vitro hyperfibrinolytic model. TXA alone delays the onset of lysis and increases clot lifetime. Treatment of clots with both TXA and HP increases clotting rate, increases maximum clot strength, and inhibits clot lysis. The results are shown in FIG. 10. Lowest (darkest) line is PBS control; second lowest is 2 μg/mL TXA; third lowest is 10 μg/mL TXA; fourth (third from top) is HP; second from top is 2 μg/mL TXA+HP; top line is 10 μg/mL TXA+HP.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A polymer comprising a plurality of repeating units forming a polymer backbone, wherein the repeating units comprise:

(a) hydrophilic repeating units; and (b) display repeating units comprising a multivalent display of fibrin-binding domains pendant at intervals along the length of the polymer.

2. The polymer of claim 1, wherein the hydrophilic repeating units are selected from the group consisting of carboxybetaines, sulfobetaines, phosphobetaines, (hydroxyethyl)methacrylate (HEMA), and N-(2-hydroxypropyl) methacrylamide (HPMA).

3. The polymer of claim 1, wherein the hydrophilic repeating units are derived from (hydroxyethyl)methacrylate (HEMA).

4. The polymer of claim 1, wherein the repeating units are present at a ratio of 4 hydrophilic repeating units to each display repeating unit.

5. The polymer of claim 1, wherein the display repeating units further comprise platelet-binding peptides and/or Von Willebrand Factor binding peptides.

6. The polymer of claim 1, wherein the fibrin-binding domains comprise polypeptides that are cyclic and comprise non-natural amino acids.

7. The polymer of claim 1, wherein the fibrin-binding domains comprise polypeptides comprising the sequence Ac-Y(DG1)C(HPr)YGLCYIQGK, wherein Ac=acetylation of N-terminus, DGI=D-glutamic acid, HPr=hydroxyproline, cyclized via C3-C8 monodisulfide bond.

8. The polymer of claim 1, which has a degree of polymerization of 200.

9. The polymer of claim 1, which has a molecular weight of 50-60 kDa.

10. The polymer of claim 1, further comprising an imaging agent bound to the polymer.

11. The polymer of claim 1, which is synthesized by reversible addition-fragmentation chain-transfer (RAFT).

12. A method of accelerating fibrin polymerization in a volume of blood, the method comprising contacting the volume of blood with the polymer of claim 1, whereby multiple binding occurs within and between fibrin fibers by the plurality of fibrin-binding domains during fibrin polymerization.

13. The method of claim 12, wherein the (CBP) bound to the polymer further comprises an agent selected from the group consisting of thrombin, tissue factor, and clotting factors.

14. A method of increasing fibrin stability in a volume of blood, the method comprising contacting the volume of blood with the polymer of claim 1, whereby multiple binding occurs within and between fibrin fibers by the plurality of fibrin-binding domains during fibrin polymerization.

15. A method of increasing clot strength in a volume of blood, the method comprising contacting the volume of blood with the polymer of claim 1, whereby multiple binding occurs within and between fibrin fibers by the plurality of fibrin-binding domains during fibrin polymerization.

16. The method of claim 12, wherein the polymer further comprises one or more clot enhancing agents bound thereto, wherein the clot enhancing agents are selected from the group consisting of antifibrinolytic drugs, platelet binding peptides, adenosine diphosphate (ADP), collagen, and von Willebrand factor.

17. A method of treating a patient suffering from a bleeding or thrombotic disorder, the method comprising administering to the subject a polymer of claim 1.

18. The method of claim 17, wherein the bleeding disorder is selected from the group consisting of: acquired platelet function defects, congenital platelet function defects, congenital protein C or S deficiency, disseminated intravascular coagulation (DIC), Factor II deficiency, Factor V deficiency, Factor VII deficiency, Factor X deficiency, Factor XII deficiency, Hemophilia A, Hemophilia B, Idiopathic thrombocytopenic purpura (ITP), and Von Willebrand's disease (types I, II, and III).

19. The polymer of claim 1, which has a molecular weight of about 5 to about 300 kDa.

20. The polymer of claim 1, which has about 8 to about 2000 repeating units.

21. The polymer of claim 1, which is a linear polymer.

22. The polymer of claim 1, which is a cyclic or branched polymer.

23. The polymer of claim 1, wherein the fibrin-binding domain is a peptide.

24. The polymer of claim 1, wherein the fibrin-binding domain is a peptide of at least 6 amino acids.

25. The polymer of claim 1, wherein the fibrin-binding domain is a peptide of at least 12 amino acids.

26. The polymer of claim 1, wherein the fibrin-binding domain is a protein fragment.

27. The polymer of claim 1, wherein the fibrin-binding domain is an aptamer.

28. The polymer of claim 1, wherein the fibrin-binding domain is a nucleic acid-based aptamer or a peptide-nucleic acid-based aptamer.

29. A pharmaceutical composition comprising the polymer of claim 1 and a pharmaceutically acceptable carrier.

* * * * *

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
```

-continued

<223> OTHER INFORMATION: modified fibrin binding peptide
<220> FEATURE:
<221> NAME/KEY: ACETYLATION
<222> LOCATION: (1)..(1)
<223> OTHER INFORMATION: acetylation of N-terminus
<220> FEATURE:
<221> NAME/KEY: SITE
<222> LOCATION: (2)..(2)
<223> OTHER INFORMATION: D-glutamic acid
<220> FEATURE:
<221> NAME/KEY: SITE
<222> LOCATION: (4)..(4)
<223> OTHER INFORMATION: hydroxyproline, cyclized via C3-C8 monodisulfide bond

<400> SEQUENCE: 1

Tyr Glu Cys Pro Tyr Gly Leu Cys Tyr Ile Gln Gly Lys
1 5 10

<210> SEQ ID NO 2
<211> LENGTH: 13
<212> TYPE: PRT
<213> ORGANISM: Artificial Sequence
<220> FEATURE:
<223> OTHER INFORMATION: modified fibrin-binding peptide
<220> FEATURE:
<221> NAME/KEY: ACETYLATION
<222> LOCATION: (1)..(1)
<223> OTHER INFORMATION: acetylation of N-terminus
<220> FEATURE:
<221> NAME/KEY: SITE
<222> LOCATION: (6)..(6)
<223> OTHER INFORMATION: D-Glutamic acid
<220> FEATURE:
<221> NAME/KEY: SITE
<222> LOCATION: (9)..(9)
<223> OTHER INFORMATION: hydroxyproline, cyclized via C3-C8 monodisulfide bond

<400> SEQUENCE: 2

Tyr Ile Cys Gly Gln Glu Ala Cys Pro Leu Tyr Gly Lys
1 5 10

<210> SEQ ID NO 3
<211> LENGTH: 12
<212> TYPE: PRT
<213> ORGANISM: Homo sapiens

<400> SEQUENCE: 3

His His Leu Gly Gly Ala Lys Gln Ala Gly Asp Val
1 5 10